US011684380B2

(12) United States Patent
Butler et al.

(10) Patent No.: US 11,684,380 B2
(45) Date of Patent: Jun. 27, 2023

(54) FORCEPS MOTION TRANSFER ASSEMBLIES

(71) Applicant: GYRUS ACMI, INC., Southborough, MA (US)

(72) Inventors: William E. Butler, Minneapolis, MN (US); Jeffrey Nelson, Plymouth, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 382 days.

(21) Appl. No.: 16/829,260

(22) Filed: Mar. 25, 2020

(65) Prior Publication Data

US 2020/0305957 A1     Oct. 1, 2020

Related U.S. Application Data

(60) Provisional application No. 62/994,220, filed on Mar. 24, 2020, provisional application No. 62/841,476, (Continued)

(51) Int. Cl.
*A61B 17/29* (2006.01)
*A61B 17/295* (2006.01)
(Continued)

(52) U.S. Cl.
CPC ........ *A61B 17/282* (2013.01); *A61B 17/1285* (2013.01); *A61B 17/2804* (2013.01); *A61B 17/285* (2013.01); *A61B 17/2833* (2013.01); *A61B 17/2909* (2013.01); *A61B 18/149* (2013.01); *A61B 18/1445* (2013.01);
(Continued)

(58) Field of Classification Search
CPC ............ A61B 17/1285; A61B 17/2804; A61B 17/2833; A61B 17/29; A61B 17/2909; A61B 18/149; A61B 90/03; A61B 18/1447; A61B 2017/2845; A61B 2017/2901; A61B 2017/2902; A61B 17/2903; A61B 2017/2908; A61B 2017/2916; A61B 2017/2917; A61B 2017/2919; A61B 2017/292; A61B 2017/2925; A61B 2017/2933; A61B 2017/2936; A61B 2017/2946; A61B 2017/320052; A61B 2018/00196; A61B 2018/0091; A61B 2090/034
See application file for complete search history.

(56) References Cited

U.S. PATENT DOCUMENTS 5,286,255 A * 2/1994 Weber ............ A61B 17/320092
606/208
5,827,279 A * 10/1998 Hughett ............. A61B 18/1447
606/205

(Continued)

*Primary Examiner* — Timothy J Neal
*Assistant Examiner* — Mitchell Brian Hoag
(74) *Attorney, Agent, or Firm* — Schwegman Lundberg & Woessner, P.A.

(57) ABSTRACT

Medical devices including a housing, an actuator, a body having a passageway extending through the body, a drive shaft extending through the passageway, and a clip coupled to the body and the drive shaft to fix the body relative to the drive shaft. The medical device further including features to couple the clip to at least one of the body and/or the drive shaft such that back out of the clip is inhibited.

20 Claims, 18 Drawing Sheets

Related U.S. Application Data filed on May 1, 2019, provisional application No. 62/826,522, filed on Mar. 29, 2019, provisional application No. 62/826,532, filed on Mar. 29, 2019.

(51) Int. Cl.
| | |
|---|---|
| *A61B 17/28* | (2006.01) |
| *A61B 18/14* | (2006.01) |
| *A61B 17/128* | (2006.01) |
| *A61B 90/00* | (2016.01) |
| *A61B 17/285* | (2006.01) |
| *B23K 26/21* | (2014.01) |
| *A61B 17/32* | (2006.01) |
| *A61B 18/00* | (2006.01) |

(52) U.S. Cl.
CPC .............. A61B 90/03 (2016.02); B23K 26/21 (2015.10); *A61B 17/29* (2013.01); *A61B 17/295* (2013.01); *A61B 18/1442* (2013.01); *A61B 18/1447* (2013.01); *A61B 2017/2845* (2013.01); *A61B 2017/2901* (2013.01); *A61B 2017/2902* (2013.01); *A61B 2017/292* (2013.01); *A61B 2017/2903* (2013.01); *A61B 2017/2908* (2013.01); *A61B 2017/2916* (2013.01); *A61B 2017/2917* (2013.01); *A61B 2017/2919* (2013.01); *A61B 2017/2925* (2013.01); *A61B 2017/2926* (2013.01); *A61B 2017/2933* (2013.01); *A61B 2017/2936* (2013.01); *A61B 2017/2945* (2013.01); *A61B 2017/2946* (2013.01); *A61B 2017/2947* (2013.01); *A61B 2017/2948* (2013.01); *A61B 2017/320052* (2013.01); *A61B 2017/320095* (2017.08); *A61B 2018/0063* (2013.01); *A61B 2018/0091* (2013.01); *A61B 2018/00148* (2013.01); *A61B 2018/00196* (2013.01); *A61B 2018/00202* (2013.01); *A61B 2018/00309* (2013.01); *A61B 2018/00345* (2013.01); *A61B 2018/00601* (2013.01); *A61B 2018/00636* (2013.01); *A61B 2018/00916* (2013.01); *A61B 2018/00946* (2013.01); *A61B 2018/00952* (2013.01); *A61B 2018/1412* (2013.01); *A61B 2018/1455* (2013.01); *A61B 2018/1457* (2013.01); *A61B 2090/034* (2016.02)

(56) References Cited

U.S. PATENT DOCUMENTS

| | | | |
|---|---|---|---|
| 6,458,130 B1 | 10/2002 | Frazier et al. | |
| 7,131,971 B2 | 11/2006 | Dycus et al. | |
| 2004/0087943 A1* | 5/2004 | Dycus ................ | A61B 17/2909 606/51 |
| 2012/0296333 A1* | 11/2012 | Twomey ............ | A61B 17/2909 606/52 |
| 2014/0025071 A1* | 1/2014 | Sims .................. | A61B 18/1482 606/46 |
| 2014/0100600 A1* | 4/2014 | Kendrick ....... | A61B 17/320092 606/205 |
| 2014/0135805 A1* | 5/2014 | Windgassen ......... | A61B 17/295 606/205 |
| 2014/0343578 A1* | 11/2014 | Huitema ............ | A61B 17/1285 606/143 |
| 2015/0196302 A1* | 7/2015 | Mazzucco .......... | A61B 17/1285 606/142 |
| 2017/0196630 A1* | 7/2017 | Nagtegaal .......... | A61B 17/2909 |
| 2017/0245921 A1* | 8/2017 | Joseph ............... | A61B 18/1445 |
| 2019/0175256 A1 | 6/2019 | Butler | |
| 2019/0298399 A1 | 10/2019 | Boone et al. | |

\* cited by examiner

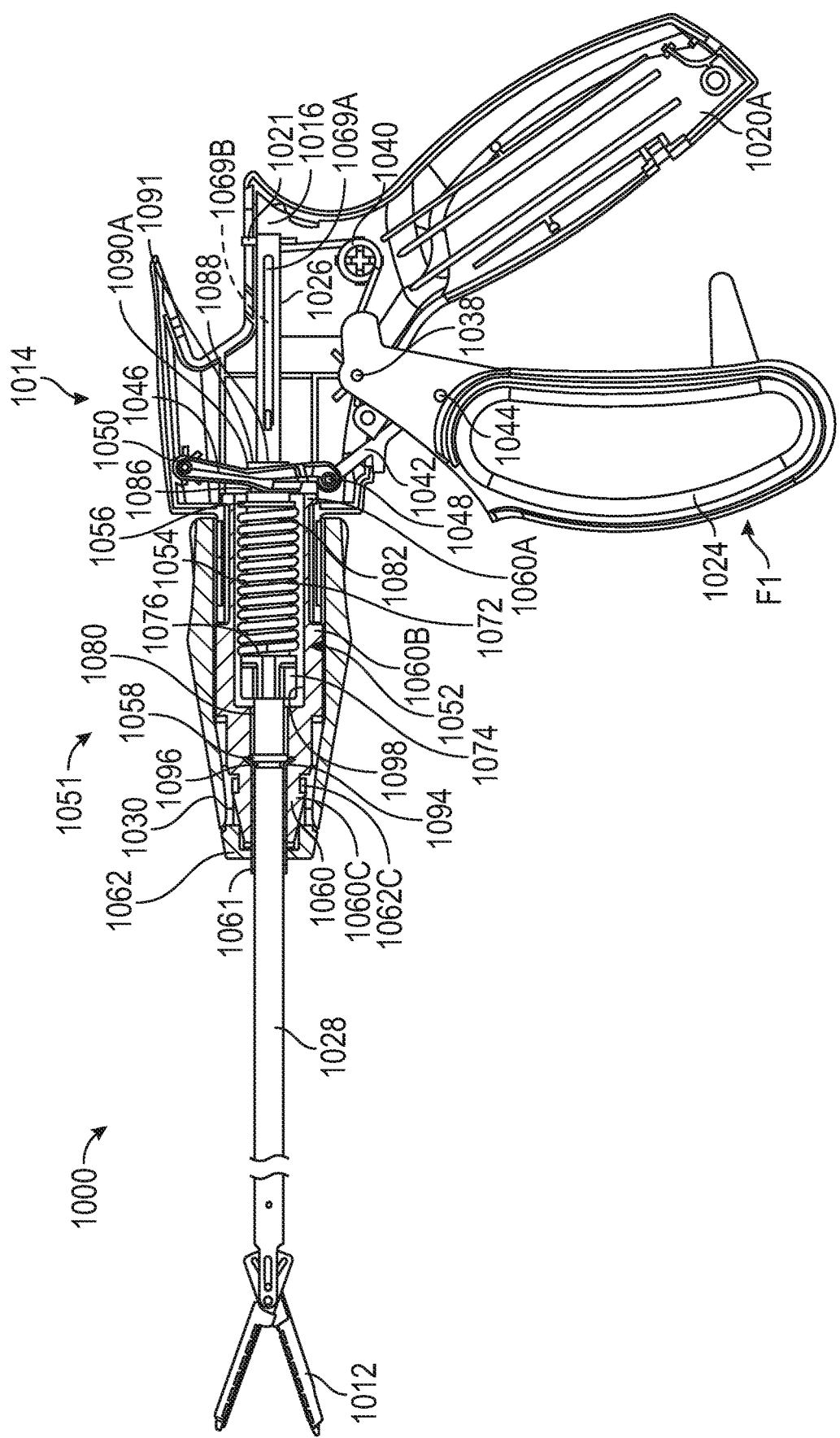

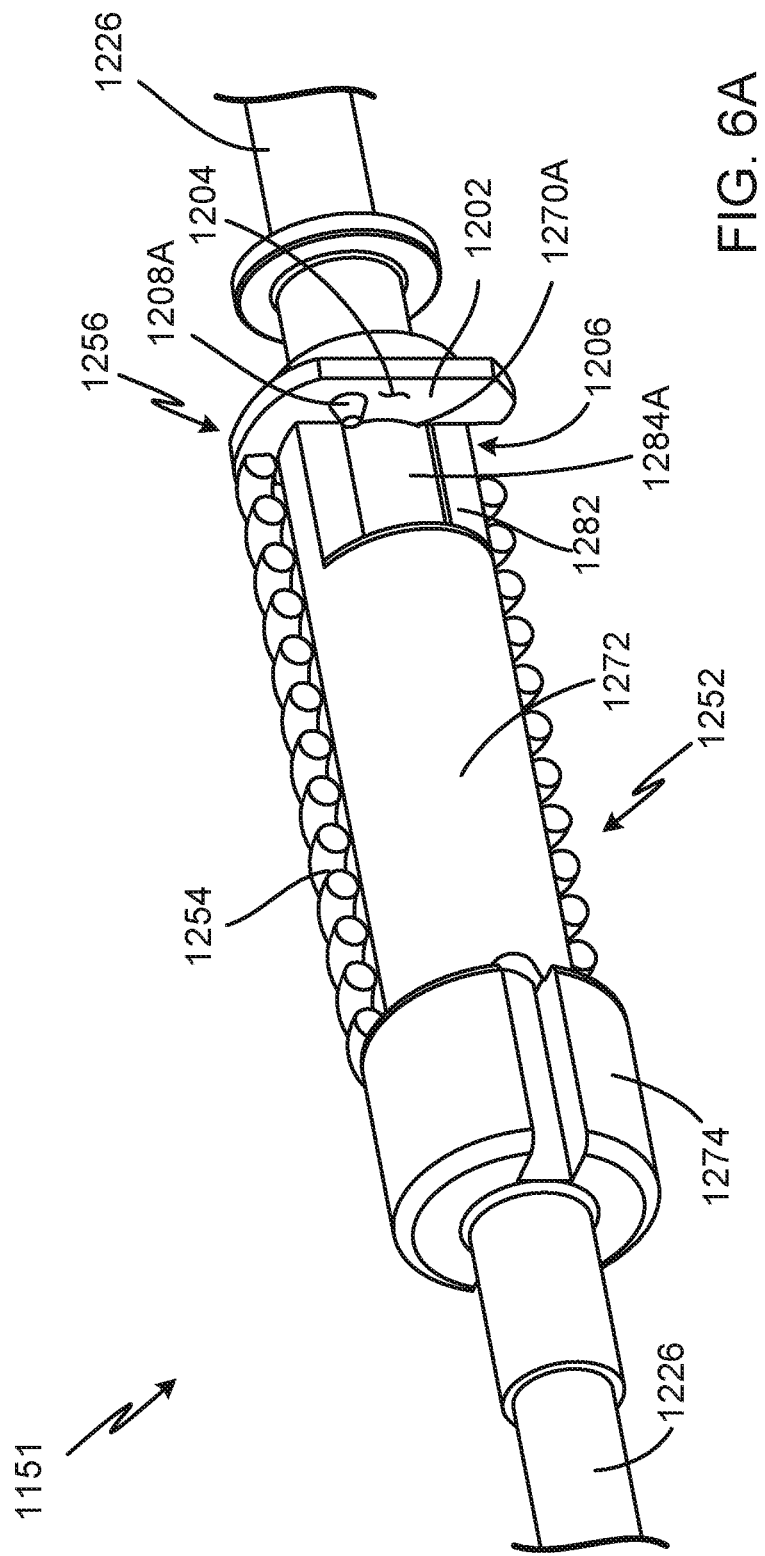

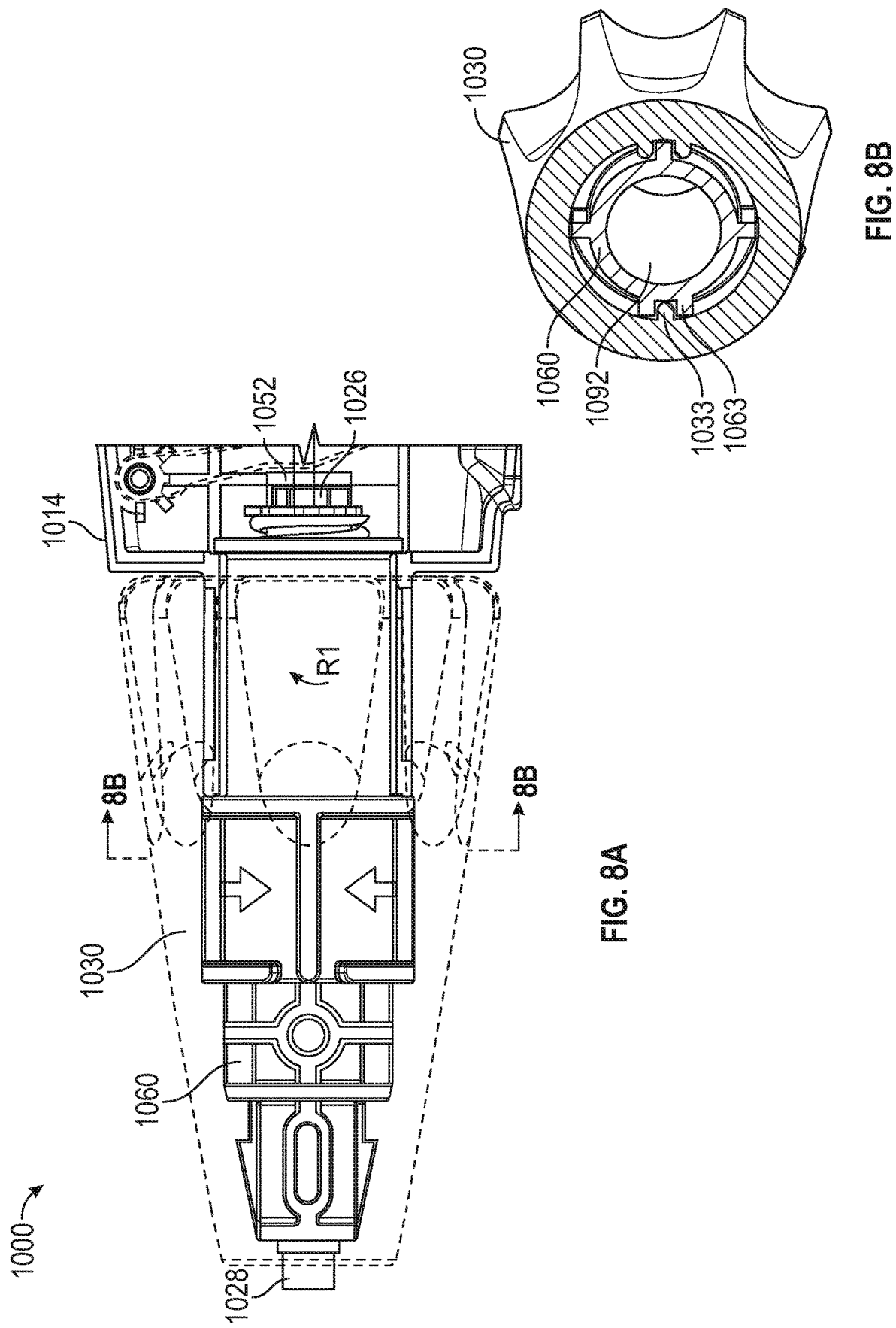

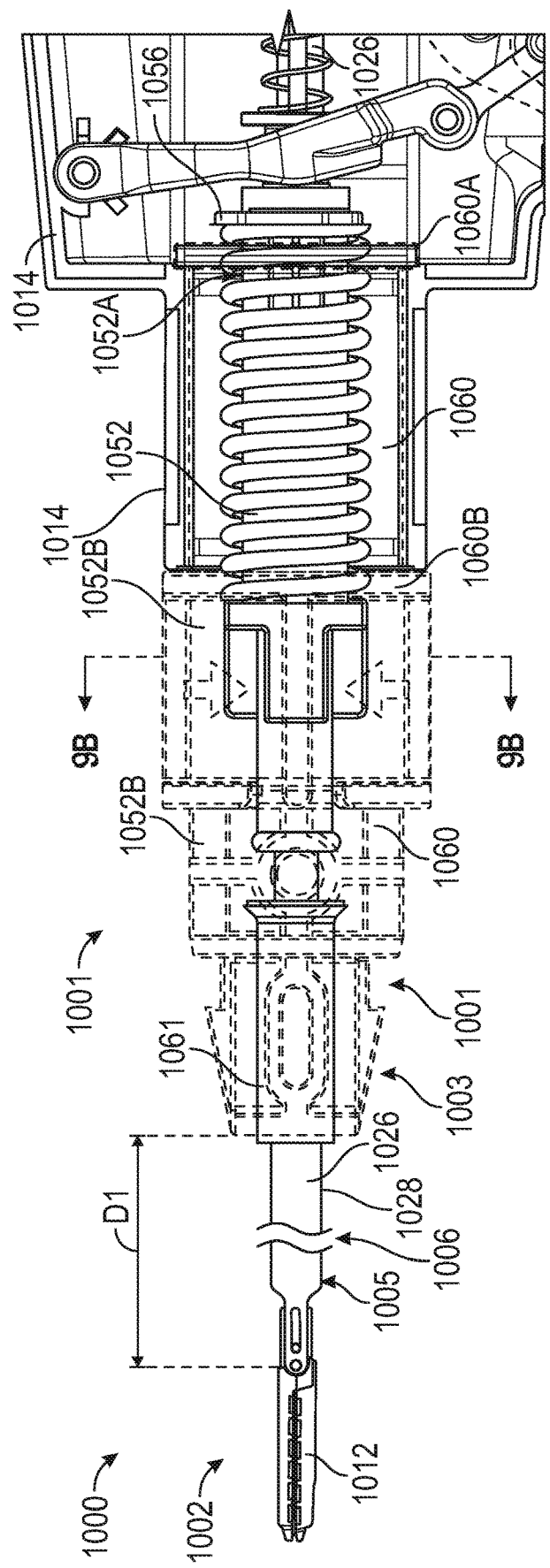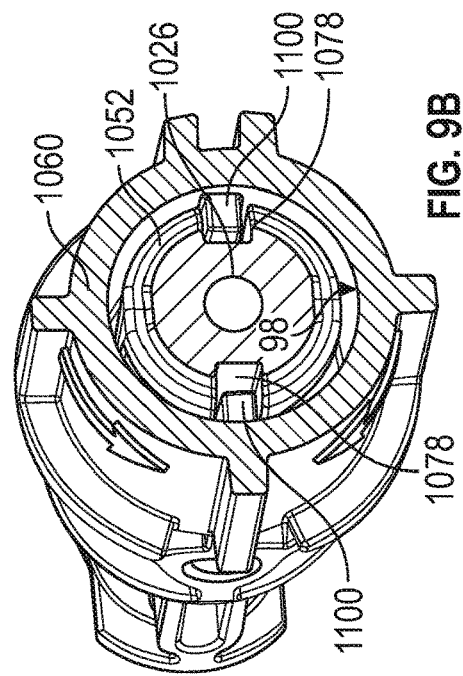

FORCEPS MOTION TRANSFER ASSEMBLIES

PRIORITY CLAIM

This application claims priority to U.S. Ser. No. 62/826,532, filed on Mar. 29, 2019, entitled "BLADE ASSEMBLY FOR FORCEPS", the disclosure of which is incorporated by reference in its entirety.

This application also claims priority to U.S. Ser. No. 62/826,522 filed on Mar. 29, 2019, entitled "SLIDER ASSEMBLY FOR FORCEPS", the disclosure of which is incorporated by reference in its entirety.

This application also claims priority to U.S. Ser. No. 62/841,476, filed on May 1, 2019, entitled "FORCEPS WITH CAMMING JAWS", the disclosure of which is incorporated by reference in its entirety.

This application also claims priority to U.S. Ser. No. 62/994,220, filed on Mar. 24, 2020, entitled "FORCEPS DEVICES AND METHODS", the disclosure of which is incorporated by reference in its entirety.

TECHNICAL FIELD

This document pertains generally, but not by way of limitation, to systems and methods for actuating end effectors of medical devices. In particular, the systems and methods can be used with a forceps having an actuatable jaw and/or a blade. The systems can include motion transfer assemblies of a handpiece that receive forces from a user and transmit the forces to an end effector to drive jaws from an open position to a closed position and to rotate the jaws.

BACKGROUND

Medical devices for diagnosis and treatment, including but not limited to forceps, are used for medical procedures such as laparoscopic and open surgeries. Forceps can be used to manipulate, engage, grasp, or otherwise affect an anatomical feature, such as a vessel or other tissue. Such medical devices can include an end effector that is one or more of: rotatable, openable, closeable, extendable, retractable and capable of supplying an input such as electromagnetic energy or ultrasound.

For example, jaws located at a distal end of a forceps are typically actuated via elements at a handpiece of the forceps to cause the jaws to open and close and thereby engage the vessel or other tissue. The jaws can also be rotationally actuated via elements at a handpiece to allow better manipulation by a user. In some cases, forceps can also include an extendable and retractable blade, such as blades that can be extended distally between a pair of jaws.

There is a need for improved medical devices, including improved actuation systems for forceps. Aspects described herein provide a variety of improvements over conventional forceps and other medical devices having a handpiece including an actuation system that controls an end effector.

SUMMARY

Illustrative examples of forceps and other surgical devices including handpieces and end effectors, are described herein.

In an example motion transfer assembly for a forceps, the motion transfer assembly includes: a body; a drive shaft; a biasing element; and a clip. The body having a passageway through the body. The drive shaft has a slot and the drive shaft extends through the passageway. The biasing element has an inner diameter positioned around the body and the clip positioned to apply a compression force to the biasing element. The clip includes a protrusion on a face abutting the biasing element, the clip is aligned with the slot, and the protrusion is located to extend within the inner diameter of the biasing element.

In an example medical device, the medical device includes: a frame, an actuator, a body, a drive shaft and a clip. The body includes a passageway through the body, and the body is configured to receive a force from the actuator. The drive shaft extends through the passageway and is coupled to the frame. The clip is coupled to the body and the drive shaft to fix the body relative to the drive shaft. Further, the clip is coupled to one of the body and the drive shaft by a resilient joint.

In a second example of a motion transfer assembly for a forceps, the motion transfer assembly includes: a body; a drive shaft; a biasing element; and a clip. The body has a passageway through the body. The drive shaft extends through the passageway. The drive shaft is slidable with respect to the body. The biasing element has an inner diameter and the biasing element positioned around the body. The clip is longitudinally and radially constrained to the drive shaft and longitudinally movable relative to the body. The clip positioned to apply a compression force to the biasing element. The clip is coupled to one of the body and the drive shaft, and one or more of the clip, the body and the drive shaft include a retention device to prevent back out of the clip relative to the body and the drive shaft.

The features described herein can be used with other devices besides forceps, such as medical devices (e.g., instruments) for performing treatment, diagnosis and imaging. The devices and methods can be employed in a variety of medical areas, including, but not limited to, general surgery, gynecology, urology, respiratory, cardiovascular, or any other suitable area.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 3A illustrates a first partial cross-section view of a portion of the forceps of FIG. 1A, in accordance with at least one example.

FIG. 6A illustrates an isometric view of a second example of a drive shaft motion transfer assembly that can be used with the forceps of FIG. 1A, in accordance with at least one example.

FIG. 8A illustrates a side view of a portion of the forceps of FIG. 1A with a rotational actuator in phantom, in accordance with at least one example.

FIG. 8B is cross-sectional view of the rotational actuator and an outer hub shown in FIG. 8A along line 8B-8B' with the rotational actuator shown in solid, in accordance with at least one example.

FIG. 9A illustrates a side view of a portion of the forceps of FIG. 1A with the outer hub shown in phantom, in accordance with at least one example.

FIG. 9B is a cross-sectional view of the outer hub and the drive body of the shown in FIG. 9A along line 9B-9B' with the outer hub shown in solid, in accordance with at least one example.

DETAILED DESCRIPTION

A medical device including a handpiece that operates an end effector allows a surgeon to control the end effector of the device to actuate one or more functions of the end effector. Actuation of the end effector can be facilitated by one or more actuation systems including a motion transfer assembly of the handpiece that can retract, extend or rotate one or more shafts to control the actions of the end effector.

The present inventors have recognized, among other things, that conventional medical devices including a handpiece that actuates an end effector can be improved to reduce packaging space, simplify design and manufacturing, improve a user's experience, increase stability and prevent damage to the forceps. In particular, there is a need to improve the actuation system which extends and retracts a drive shaft and a need to manage an excessive force from being transmitted from an actuator to the end effector (e.g., a force-limiting capability). There is also a need to improve transmission of a rotational force from a rotational actuator to an end effector.

This disclosure is generally related to medical devices, such as surgical instruments. Although the present application is described with reference to a forceps, other end effectors can be used with and operated by the handpiece described herein. In addition, other handpieces can be connected to and can control the end effectors described herein. This disclosure includes examples of handpieces including one or more actuation systems, examples of end effectors, and examples where the disclosed actuation systems and end effectors can be used together in a medical device.

The forceps can include a medical forceps, a cutting forceps, an electrosurgical forceps, or any other type of forceps. The forceps can include an end effector that is controlled by a handpiece including an actuation system to be one or more of: rotatable, openable and closeable. For example, jaws located at a distal end of the forceps can be actuated via one or more actuators at a handpiece of the forceps to cause the jaws to open, close and rotate to engage a vessel or other tissue. Although this disclosure focuses on the open, close and rotation aspects of the jaws of the forceps, the forceps may also include an extendable and retractable blade, such as blades that can be extended distally in between a pair of jaws to separate a first tissue from a second tissue. The end effector can also be capable of supply electromagnetic energy or ultrasound to the tissue.

Figure 1A:
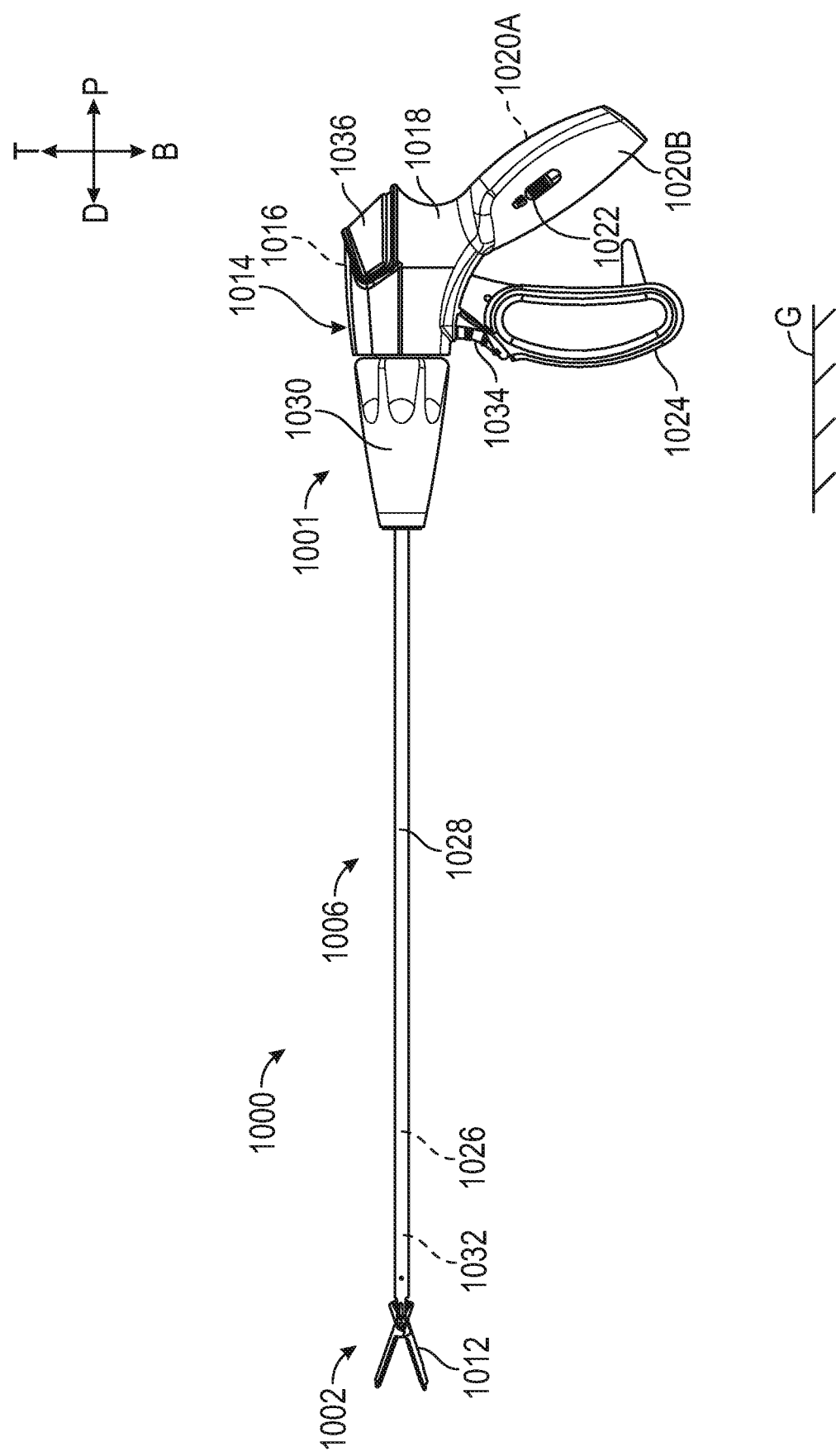
FIG. 1A illustrates a side view of a forceps showing jaws in an open position, in accordance with at least one example.
Figure 1B:
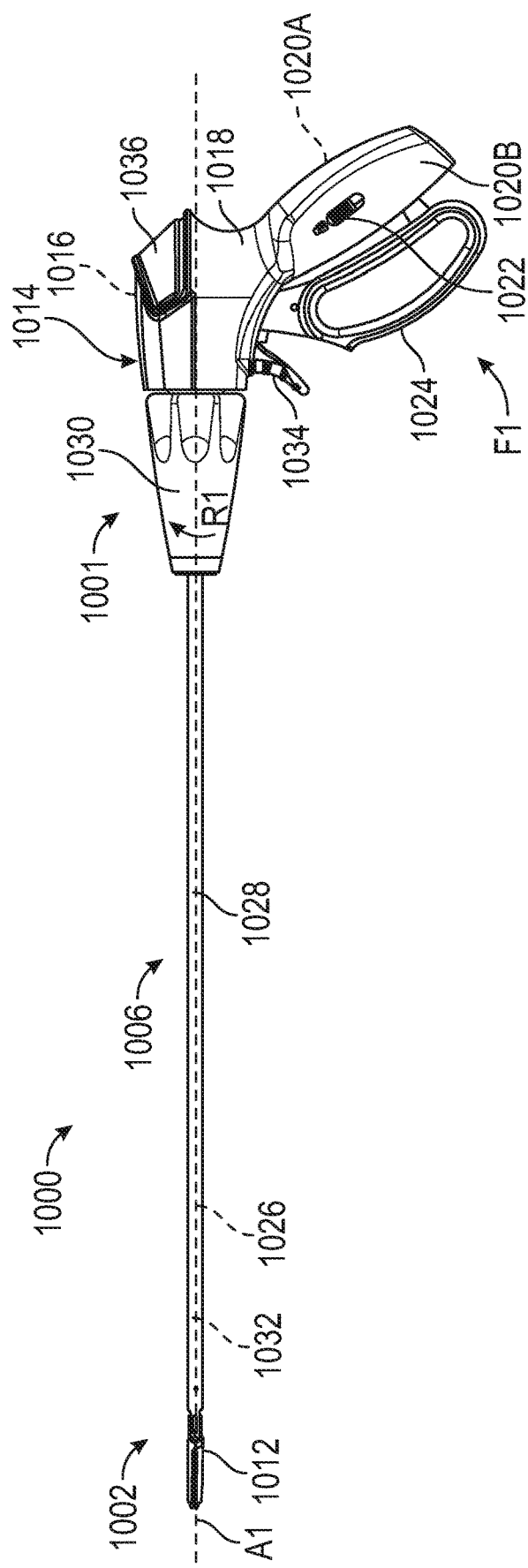
FIG. 1B illustrates a side view of the forceps of FIG. 1A showing the jaws in a closed position, in accordance with at least one example.
Figure 2:
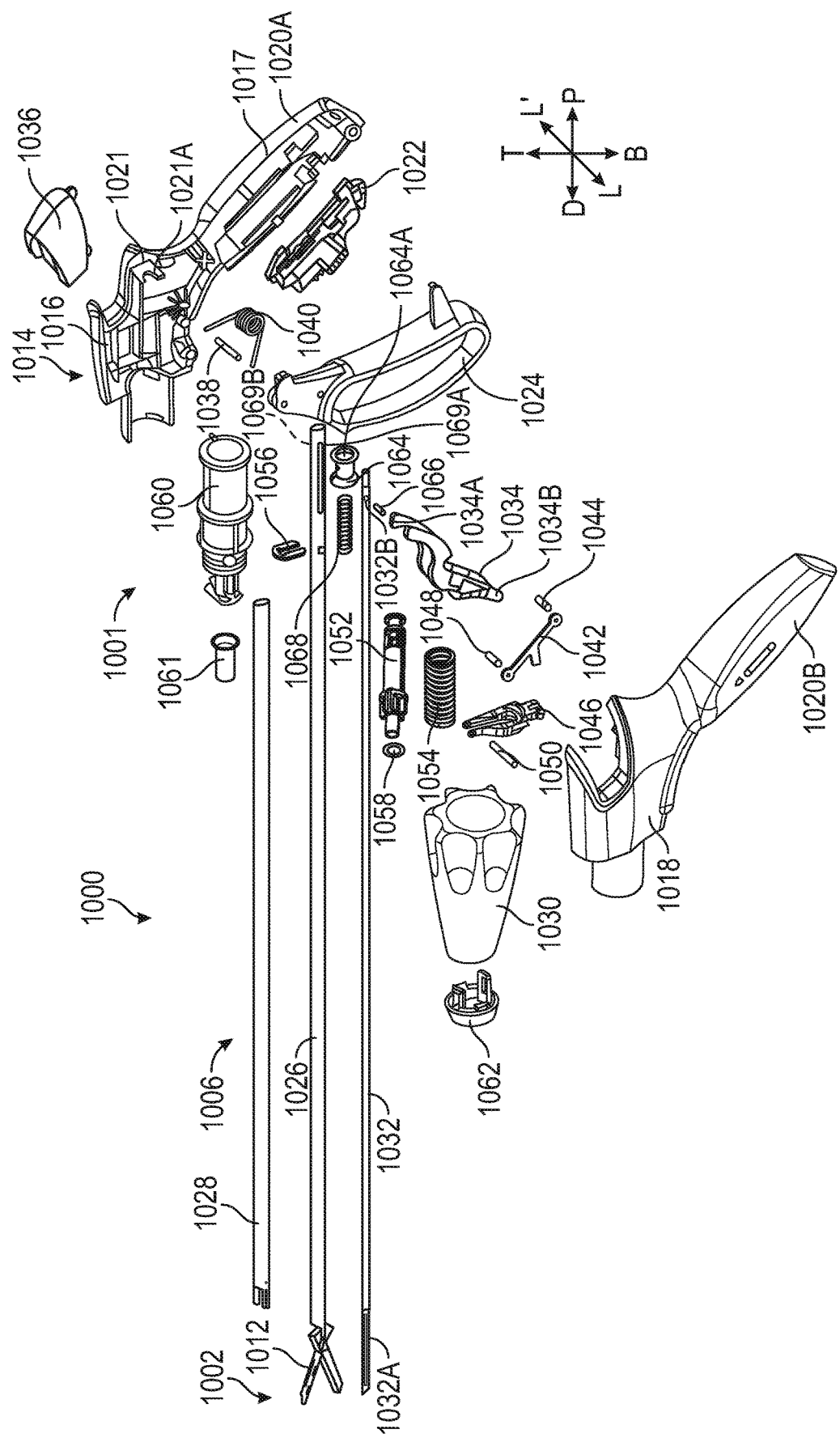
FIG. 2 illustrates an exploded view of some components of the forceps of FIG. 1A, in accordance with at least one example.

FIG. 1A illustrates a side view of a forceps 1000 with jaws 1012 in an open position. FIG. 1B illustrates a side view of the forceps 1000 with the jaws 1012 in a closed position. FIG. 2 illustrates an exploded view of some components of the forceps 1000 of FIG. 1A. FIGS. 1A, 1B and 2 are described together. Directional descriptors such as proximal and distal are used within their ordinary meaning in the art. The proximal direction P and distal direction D are indicated on the axes provided in FIG. 1A and FIG. 2. FIG. 2 also shows the lateral directions L and L', as well as top T and bottom B directions, which are defined when the forceps 1000 is held level with respect to a ground G in an upright orientation as shown in FIG. 1A. Opposite to the lateral directions L and L', is the medial direction, in other words, the medial direction is towards the centerline, or longitudinal axis A1 of the forceps 1000 (FIG. 1B).

The illustrative forceps 1000 can include a handpiece 1001 at a proximal end, and an end effector 1002 at a distal end. An intermediate portion 1006 can extend between the handpiece 1001 and the end effector 1002 to operably couple the handpiece 1001 to the end effector 1002. Various movements of the end effector 1002 can be controlled by one or more actuation systems of the handpiece 1001. In the illustrative example, the end effector 1002 can include the jaws 1012 that are capable of opening and closing. The end effector 1002 can be rotated along a longitudinal axis A1 (FIG. 1B) of the forceps 1000. The end effector 1002 can include a cutting blade 1032A (FIG. 2) and an electrode for applying electromagnetic energy. All actuation system functions and all end effector actions are not required in all examples. The functions described herein can be provided in any combination.

An overview of features of the forceps 1000 is provided in FIGS. 1A, 1B, 2, 3A-3E and 4A-4C. Further detailed illustration of example motion transfer assemblies is provided in FIGS. 5A, 5B, 6A, 6B, 7A, 8A, 8B, 9A and 9B. The illustrated motion transfer assemblies provide transmission of forces received from a user via clamping and rotational actuators (e.g., a lever 1024 and a rotational actuator 1030), to the jaws 1012 of the forceps 1000 to actuate clamping and rotation of the jaws 1012.

As shown broadly in FIGS. 1A and 1B, with support from FIG. 2, the forceps 1000 can include the jaws 1012, a housing 1014, the lever 1024, a drive shaft 1026, an outer shaft 1028, the rotational actuator 1030, a blade assembly (a blade shaft 1032 and a blade 1032A of FIG. 2), a trigger 1034 and an activation button 1036. In this example, the end effector 1002, or a portion of the end effector 1002, such as the jaws 1012 can be one or more of: opened, closed and rotated. In some examples, the end effector 1002, such as the blade 1032A of the end effector 1002, can be extended or retracted, and the jaws 1012 can be electromagnetically energized (e.g., electrically energized). In some examples, the energy can be radio-frequency energy.

To operate the end effector 1002, the user can displace the lever 1024 proximally by applying an input force F1 (FIG. 1B) to drive the jaws 1012 from the open position (FIG. 1A) to the closed position (FIG. 1B). In the example of forceps 1000, moving the jaws 1012 from the open position to the closed position allows a user to clamp down on and compress a tissue. The handpiece 1001 can also allow a user to rotate the end effector 1002. For example, rotating rotational actuator 1030 (e.g., a user applying a rotational input R1, FIG. 1B) causes the end effector 1002 to rotate by rotating both the drive shaft 1026 and the outer shaft 1028 together.

In some examples, with the tissue compressed between the jaws 1012, a user can depress the activation button 1036 to cause an electrical energy, such as an electromagnetic energy, to be delivered to the end effector 1002, such as to an electrode of the jaws 1012. Application of electromagnetic energy can be used to seal or otherwise affect the tissue being clamped. In some examples, the electromagnetic energy can cause tissue to be coagulated, cauterized, sealed, ablated, desiccated or can cause controlled necrosis. Example electrodes are described herein, but electromagnetic energy can be applied to any suitable electrode.

The handpiece 1001 can enable a user to extend and retract a blade 1032A attached to a distal end of a blade shaft 1032 (FIG. 2). The blade 1032A can be extended by displacing the trigger 1034 proximally. The blade 1032A can be retracted by allowing the trigger 1034 to return distally to a default position. The default position of the trigger 1034 is shown in FIG. 1A. In some examples, as described herein, the handpiece 1001 can include features that inhibit the blade 1032A from being extended until the jaws 1012 are at least partially closed, or fully closed.

The forceps 1000 can be used to perform a treatment on a patient, such as a surgical procedure. In an example, a distal portion of the forceps 1000, including the jaws 1012, can be inserted into a body of a patient, such as through an incision or another anatomical feature of the patient's body. While a proximal portion of the forceps 1000, including housing 1014 remains outside the incision or another anatomical feature of the body. Actuation of the lever 1024 causes the jaws 1012 to clamp onto a tissue. The rotational actuator 1030 can be rotated via a user input to rotate the jaws 1012 for maneuvering the jaws 1012 at any time during the procedure. Activation button 1036 can be actuated to provide electrical energy to jaws 1012 to coagulate, cauterize or seal the tissue within the closed jaws 1012. Trigger 1034 can be moved to translate the blade 1032A distally to cut the tissue within the jaws 1012.

In some examples, the forceps 1000, or other medical device, may not include all the features described or may include additional features and functions, and the operations may be performed in any order. The handpiece 1001 can be used with a variety of other end effectors to perform other methods.

As shown in the combination of FIG. 1A, FIG. 1B and FIG. 2, the forceps 1000 can include various components. For example, a first housing portion 1016 and a second housing portion 1018. As shown in FIG. 2, the first housing portion 1016 and the second housing portion 1018 can mate at a coupling joint 1017. The housing 1014 can include, or be coupled to, a handle portion 1020A and 1020B, such as a fixed handle that is configured to be held in the hand of a user during use. The housing 1014 can be a frame that provides structural support between components of the forceps 1000. The housing 1014 is shown as housing at least a portion of the actuation systems associated with the handpiece 1001 for actuating the end effector 1002.

With continued reference to FIG. 1A, FIG. 1B and FIG. 2, the drive shaft 1026 can extend through the housing 1014 and out of a distal end of the housing 1014, or distally beyond housing 1014. The jaws 1012 can be connected to a distal end of the drive shaft 1026. The outer shaft 1028 can be a hollow tube positioned around the drive shaft 1026. A distal end of the outer shaft 1028 can be located adjacent the jaws 1012 and the jaws 1012 can be connected to the outer shaft 1028. The distal ends of the drive shaft 1026 and the outer shaft 1028 can be rotationally locked (e.g., rotationally constrained) to the jaws 1012. The rotational actuator 1030 can be positioned around the distal end of the housing 1014. In the illustrative example, the rotational actuator 1030 is indirectly connected to a proximal end of the outer shaft 1028 by an outer hub 1060, however, in some examples the rotational actuator 1030 can be directly connected to the proximal end of the outer shaft 1028 or can integrally include the features of the outer hub 1060. In some examples, various rotational constraints described herein can be employed independently. In other words, some examples can employ a single rotational constraint between the rotational actuator 1030 and the jaws 1012, while in other examples, the rotational constraint can include multiple rotational constraints at different locations along the longitudinal axis A1, such as a first rotational constraint proximate or within the handpiece 1001, and a second rotational constraint proximate the end effector 1002 and distal of the handpiece 1001.

The outer shaft 1028 can extend distally beyond the rotational actuator 1030. The blade shaft 1032 can extend through the drive shaft 1026 and the outer shaft 1028. A distal end of the blade shaft 1032 including the blade 1032A can be located adjacent to the jaws 1012. A proximal end of the blade shaft 1032 can be within the housing 1014.

A proximal portion 1034A (FIG. 2) of the trigger 1034 can be connected to the blade shaft 1032 within the housing 1014. A distal portion 1034B (FIG. 2) of the trigger 1034 can extend outside of the housing 1014 adjacent, and in some examples, nested with the lever 1024 in the default or unactuated positions shown in FIG. 1A. Activation button 1036 can be coupled to the housing 1014. Activation button 1036 can actuate electronic circuitry within housing 1014 that can send electromagnetic energy through forceps 1000 to the jaws 1012. When the user presses on the activation button 1036, the activation button 1036 can move relative to the housing 1014.

As shown in the exploded view of a portion of the forceps 1000 in FIG. 2, the forceps 1000 can include the handpiece 1001 having components for an actuation system, the end effector 1002, the intermediate portion 1006, the jaws 1012, the housing 1014 (including the first housing portion 1016, the second housing portion 1018, the handle portion 1020A and 1020B, the stabilizing flange 1021, and a recess or an opening 1021A), the handle locking mechanism 1022, the lever 1024, the drive shaft 1026 (including the first horizontal slot 1069A and the second horizontal slot 1069B, the outer shaft 1028, the rotational actuator 1030, the blade shaft 1032, the blade 1032A the trigger 1034, and the activation button 1036, a first pin 1038, a lever return spring 1040, a coupling link 1042, a second pin 1044, a drive link 1046, a third pin 1048, a fourth pin 1050, a drive shaft motion transfer body 1052 (hereinafter, drive body 1052), a force-limiting spring 1054, a clip 1056, an O-ring 1058, an outer hub 1060, a nose 1062, a spool 1064, a cross pin 1066 (e.g., a blade pin), and a trigger return spring 1068. The handle locking mechanism 1022 can be, for example, of the type described in U.S. patent application Ser. No. 15/941,205 to Boone, titled "Forceps Including a Pre-loaded Handle Latch" filed on Mar. 30, 2018, the disclosure of which is incorporated by reference in its entirety. Furthermore, the components which make up the actuation system can be, for example, of the type described in U.S. patent application Ser. No. 15/839,218 to Butler titled "Laparoscopic Forceps Assembly with An Operable Mechanism" filed on Dec. 12, 2017, the disclosure of which is incorporated by reference in its entirety.

As a general overview of the component interaction of the handpiece 1001 of the forceps 1000, the forceps 1000 can include the drive body 1052 being constrained to the drive shaft 1026 to transfer motion to the drive shaft 1026, thereby operating the jaws 1012. However, in a force limiting state, the drive body 1052 can be slidable with respect to the drive shaft 1026. Thus, the forceps 1000 can be configured to limit a force on the jaws 1012 to protect the jaws 1012 from damage when the lever 1024 is being closed with the jaws 1012 stuck in an open or partially open position. An example of the jaws 1012 stuck in such a position is shown in FIG. 4C.

As further shown and described herein, the drive body 1052 along with the clip 1056 can lock the drive shaft 1026 to the rotational actuator 1030 such that the drive shaft 1026 and the outer shaft 1028 are rotationally locked (e.g., rotationally constrained) together at a proximal portion of the drive shaft 1026 and the outer shaft 1028 proximate the rotational actuator 1030. Further, the forceps 1000 can include the trigger 1034, the spool 1064 proximal to the drive body 1052 and connected to the trigger 1034, and a trigger return spring 1068 positioned between the drive body 1052 and the spool 1064 to bias the blade shaft 1032 with blade 1032A proximally but allow movement of the blade 1032A distally to perform a cut, while improving the design of the forceps.

FIGS. 3A, 3B, 3C, 3D and 3E focus on the clamping and rotational aspects of the forceps and will be described together with support from FIGS. 1A, 1B and 2. Many of these components are introduced here, but also shown and described in further detail in other figures herein.

Figure 3B:
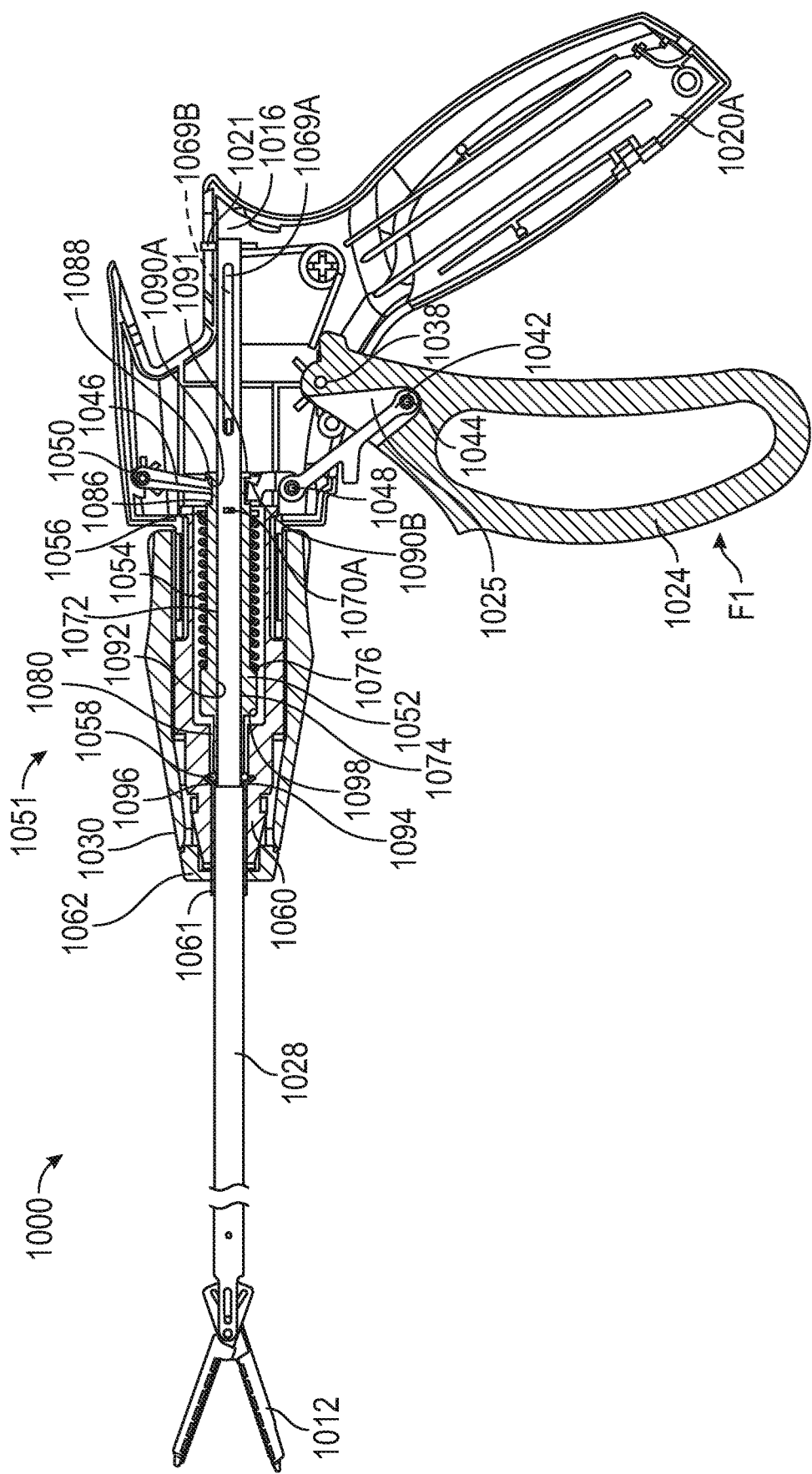
FIG. 3B illustrates a second partial cross-section view of a portion of the forceps of FIG. 1A, in accordance with at least one example.
Figure 3C:
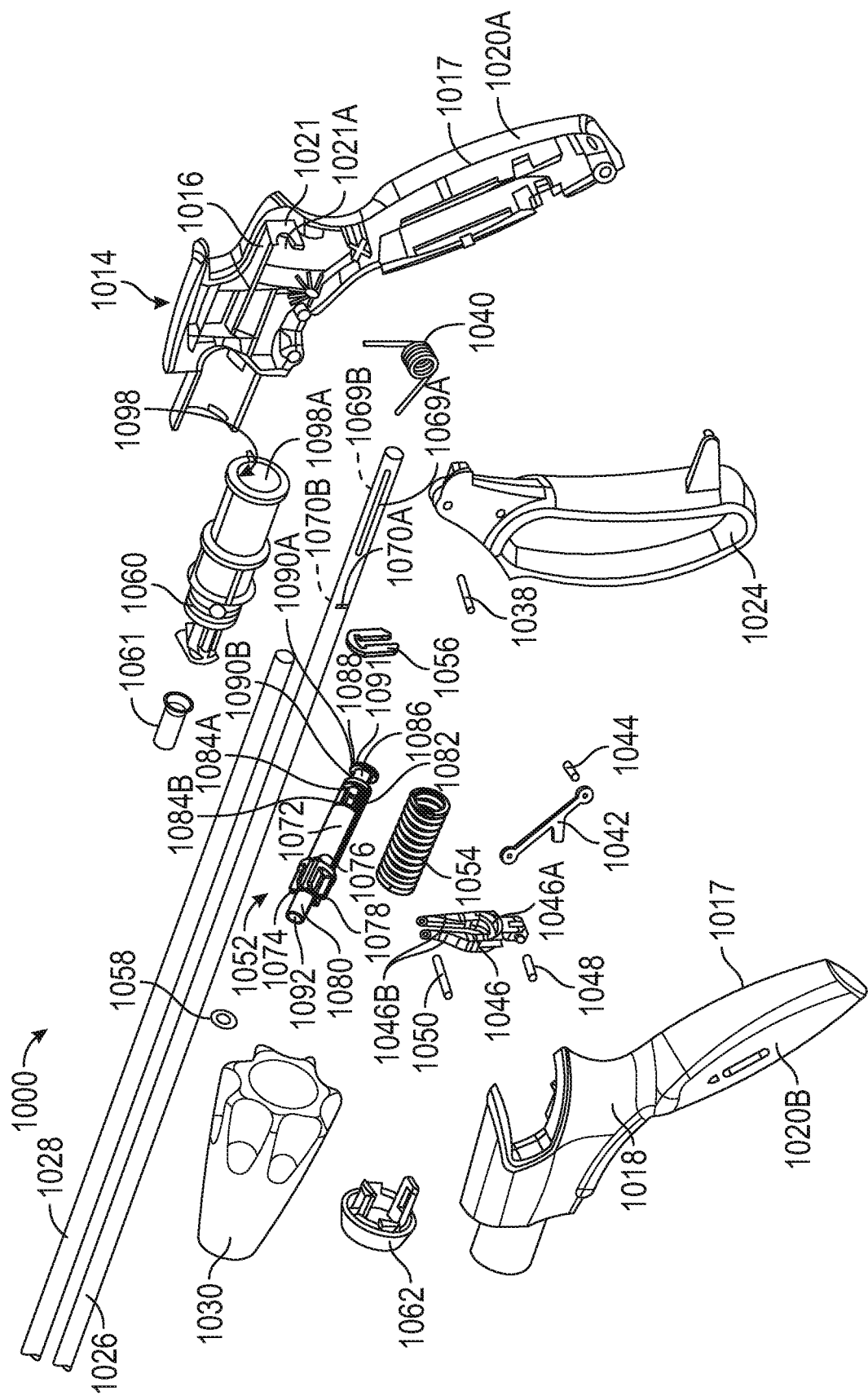
FIG. 3C illustrates a close-up exploded view of a portion of the forceps of FIG. 1A, in accordance with at least one example.
Figure 3D:
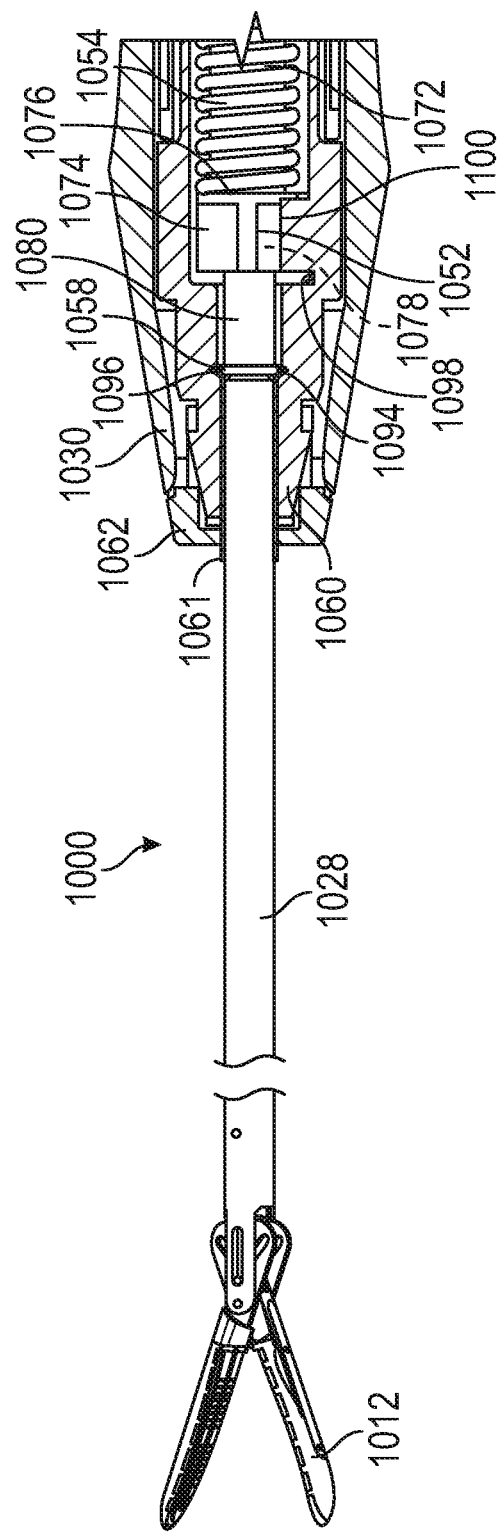
FIG. 3D illustrates a third partial cross-section view of the forceps of FIG. 3A showing a drive shaft motion transfer body in a rotated position, in accordance with at least one example.
Figure 3E:
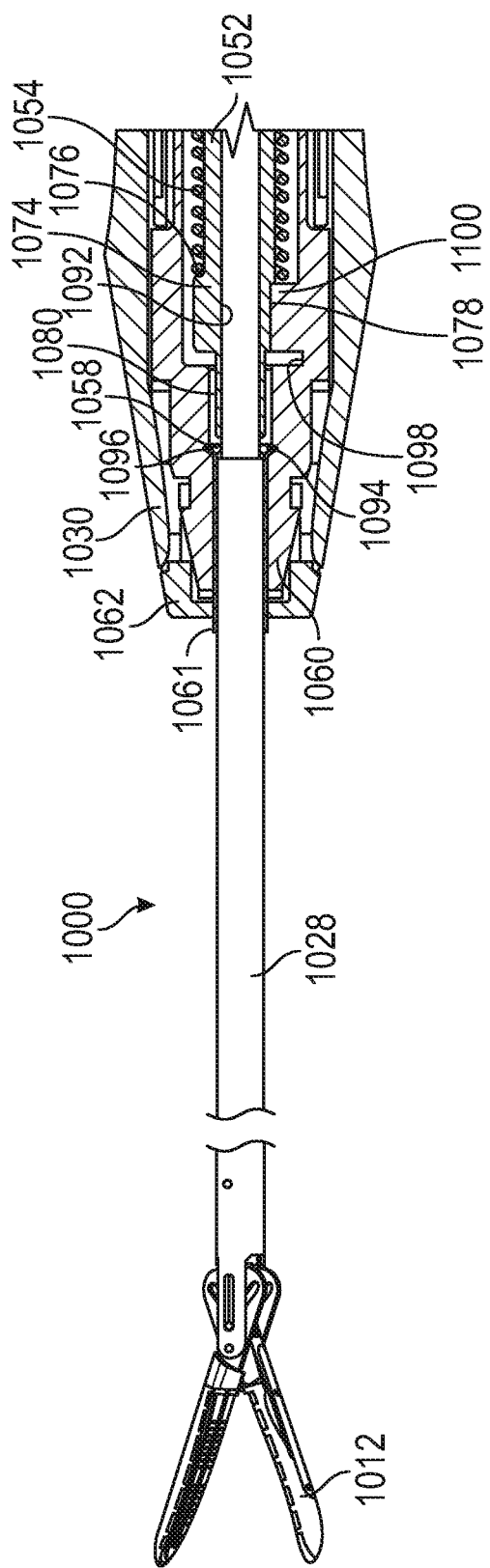
FIG. 3E illustrates a fourth partial cross-section view of the forceps of FIG. 3A showing the drive shaft motion transfer body in the rotated position of FIG. 3D, in accordance with at least one example.

FIG. 3A illustrates a first partial cross-section view of a portion of the forceps 1000 of FIG. 1A, FIG. 1B and FIG. 2, in accordance with at least one example. The lever 1024, the drive shaft 1026, the drive body 1052, the force-limiting spring 1054, the clip 1056, the O-ring 1058 and the outer shaft 1028 are not shown in cross section. FIG. 3B illustrates a second partial cross-section view of a portion of the forceps 1000, in accordance with at least one example. The drive shaft 1026 and the outer shaft 1028 are not shown in cross-section. FIG. 3C illustrates a close-up exploded view of a portion of the forceps 1000 of FIG. 1A, in accordance with at least one example. FIG. 3D illustrates a third partial cross-section view of the forceps 1000 of FIG. 3A showing the drive body 1052 in a rotated position, in accordance with at least one example. The drive body 1052, the force-limiting spring 1054, the O-ring 1058, and the outer shaft 1028 are not shown in cross-section. FIG. 3E illustrates a fourth partial cross-section view of the forceps 1000 of FIG. 3A showing the drive body 1052 in the rotated position of FIG. 3D, in accordance with at least one example. The outer shaft 1028 is not shown in cross section.

FIGS. 3A, 3B, 3C, 3D and 3E, described together with most components shown in the exploded view of FIG. 3C, include the housing 1014 (including the first housing portion 1016, the handle portion 1020A, and the stabilizing flange 1021), the lever 1024, the first pin 1038, the drive shaft 1026, the lever return spring 1040, the coupling link 1042 can reside within a lever recess 1025, the second pin 1044, the drive link 1046, the third pin 1048, the fourth pin 1050, a drive motion transfer assembly 1051, the drive body 1052, the force-limiting spring 1054, the clip 1056, the O-ring 1058, the outer shaft 1028, the outer hub 1060, a sleeve 1061, the rotational actuator 1030, and the nose 1062. The drive shaft 1026 includes the first horizontal slot 1069A, the second horizontal slot 1069B, a first vertical slot 1070A, and a second vertical slot 1070B, which can be an opening extending through the drive shaft 1026, or a recess or deformation in the drive shaft 1026. The drive body 1052 (shown in further detail in other drawings herein) can include a body portion 1072, an anchor portion 1074 (including a distal spring seat 1076 and a rotational keying slot 1078), a cylindrical portion 1080, a window portion 1082 (including a first window 1084A and a second window 1084B, see FIG. 3C), a neck portion 1086, a collar 1088 (such as proximal collar 1088 including a drive surface 1090A and a second distal spring seat 1091, see FIGS. 3B and 3C, as well as FIG. 5A for a close-up view), and a passageway 1092 (e.g. a channel, a bore, a recess, or an aperture extending therethrough). The sleeve 1061 can include a flange 1094. In some examples, such as an example where the sleeve 1061 is omitted, the outer shaft 1028 can include the flange 1094. The outer hub 1060 can include groove 1096, interior surface 1098, and the anti-rotation key 1100 (FIGS. 3D and 3E).

The first and second horizontal slots 1069A, 1069B can extend longitudinally along the drive shaft 1026, in an axial direction, parallel to longitudinal axis A1 (FIG. 1B). In other words, the first and second horizontal slots 1069A, 1069B can be described as extending horizontally when the drive shaft 1026 is held level. In some examples, the first and second vertical slots 1070A may extend along or within a plane perpendicular to the longitudinal axis A1.

Figure 5A:
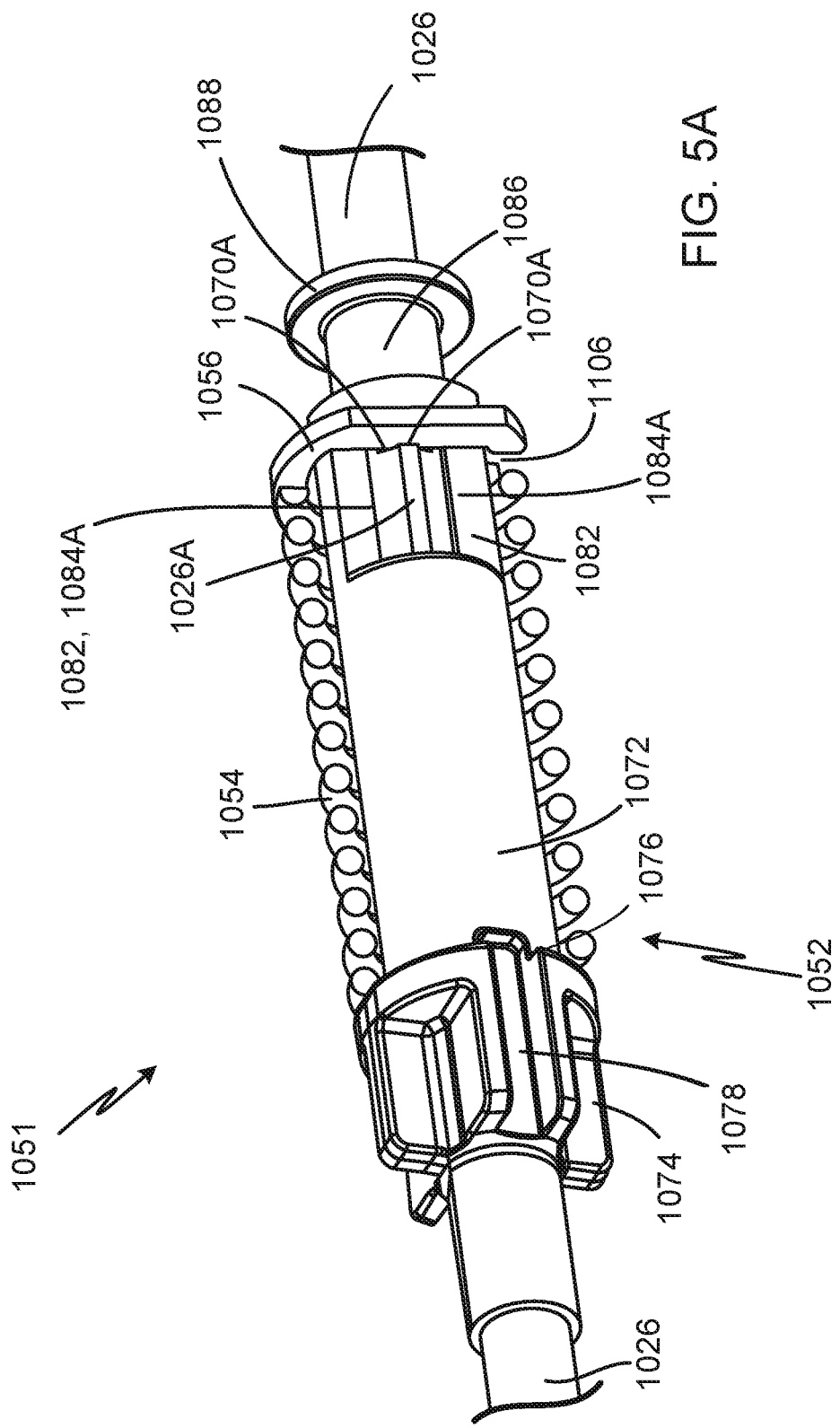
FIG. 5A illustrates an isometric view of an example of a drive shaft motion transfer assembly that can be used with the forceps of FIG. 1A, in accordance with at least one example.
Figure 5B:
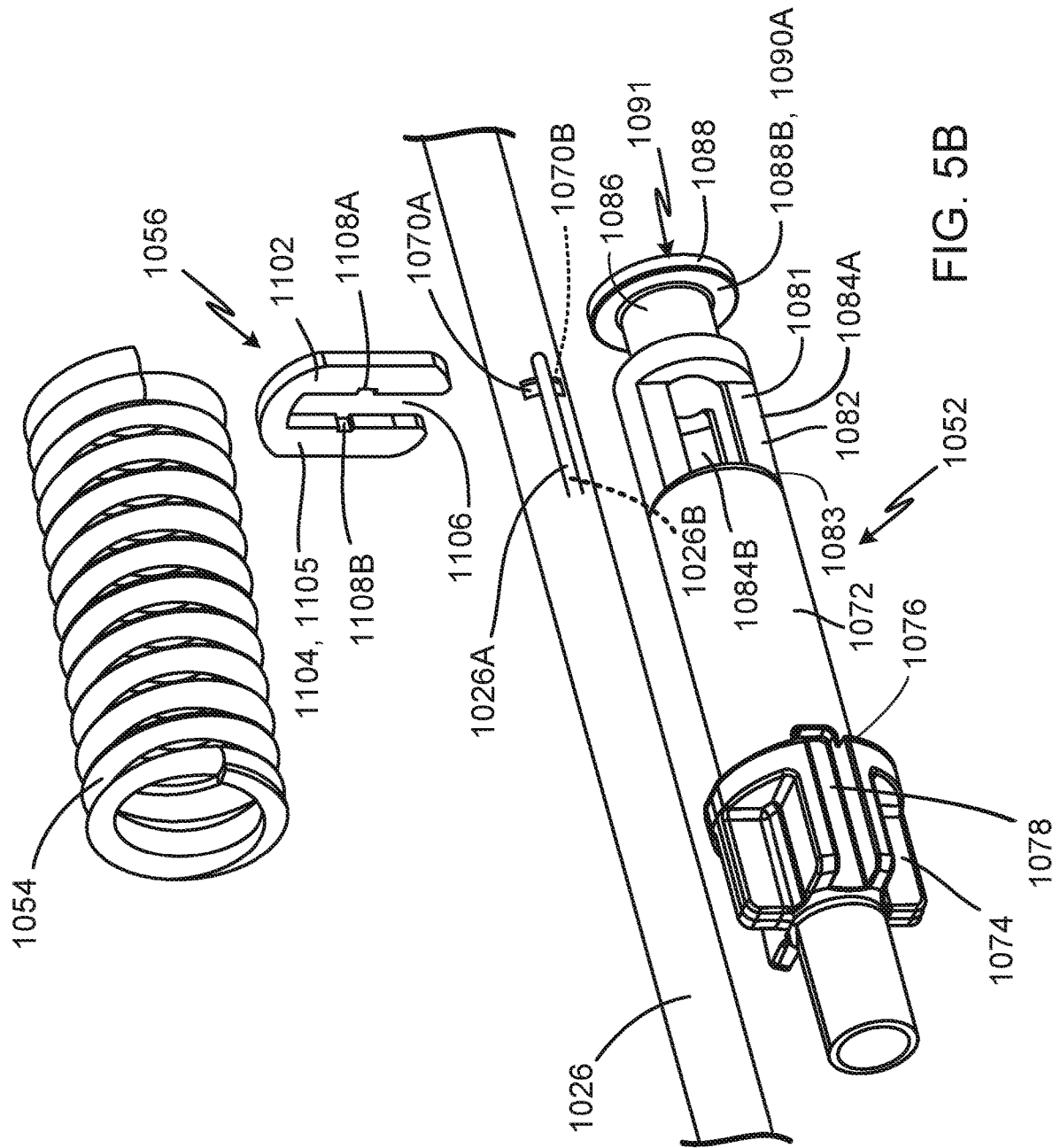
FIG. 5B illustrates an exploded view of the example of the drive shaft motion transfer assembly of FIG. 5A, in accordance with at least one example.

The drive shaft 1026 can include the first vertical slot 1070A on a first side and the second vertical slot 1070B on a second side (FIG. 3B, 3C, further shown and described in FIGS. 5A and 5B). The vertical slots 1070A and 1070B can be perpendicular to the longitudinal axis A1 (FIG. 1B) of drive shaft 1026. The first vertical slot 1070A and second vertical slot 1070B can extend into the drive shaft 1026 from an exterior surface of the drive shaft 1026. The first vertical slot 1070A and the second vertical slot 1070B can be sized to accept the clip 1056. In some examples, the clip 1056 can be ridged and can be accepted onto the drive shaft 1026 without distorting the shape of the clip 1056, however, in other examples, the clip 1056 may be a flexible type that is capable of some distortion during assembly. In some examples, the drive shaft 1026 can have a single vertical slot 1070A or 1070B. The first and second vertical slots 1070A, 1070B can be provided as an opening/aperture or as a deformation with or without an opening through the drive shaft 1026.

As shown in the combination of FIGS. 3A-3E, and in close-up views of FIGS. 5A and 5B, the drive body 1052 can include the body portion 1072 and the anchor portion 1074 connected, or integrally formed, at distal end of the body portion 1072. The anchor portion 1074 can extend outwardly from an outer surface of body portion 1072. As such, the anchor portion 1074 can include the distal spring seat 1076 at a proximal end surface of the anchor portion 1074. The distal spring seat 1076 can be connected to a distal end of the body portion 1072.

As shown in FIGS. 3C, 3D and 3E, and as shown in further detail in other figures herein, including some features shown close-up in FIG. 5A, the anchor portion 1074 can include the rotational keying slot 1078. The rotational keying slot 1078 is also shown close-up in FIG. 5B and FIG. 9B. The rotational keying slot 1078 can be horizontal slot, or a slot extending parallel to the longitudinal axis A1 of the drive shaft 1026 (A1 is shown in FIG. 1B). The rotational keying slot 1078 can extend into a side of the body portion 1072. In alternate examples, the drive body 1052 may have any number of the rotational keying slot(s) 1078. In some examples, the rotational keying slot 1078 can be any other suitable keying interface known in the art and are not necessarily provided as a slot. The interaction between the rotational keying slot 1078 and an anti-rotation key 1100 of the outer hub 1060 is further described herein. The rotational keying slot 1078 and the anti-rotation key 1100 on the outer hub 1060 can be any type of interface that limits relative rotation between the drive body 1052 and the outer hub 1060. For example, the rotational keying slot 1078 can be a protrusion instead of a slot to be received by the anti-rotation key 1100 that is a slot, recess or groove of the outer hub 1060 in order to provide the relative anti-rotation features between the drive body 1052 and the outer hub 1060.

The cylindrical portion 1080 of the drive body 1052 can be connected to, or integrally formed with, the distal end of the anchor portion 1074. The cylindrical portion 1080 can be sized to accept the O-ring 1058.

As shown in the exploded view of FIG. 3C, and in more detail in other figures herein, the window portion 1082 can include the first window 1084A extending through the first side of body portion 1072 and the second window 1084B opposite the first window 1084A and extending through the second side of body portion 1072. Although described as a window, in some examples the window portion 1082 may be provided as a track, such a window or track need not necessarily be bounded on all sides, and sections of the window or track may not extend entirely through the body portion 1072.

As shown in FIGS. 3A, 3B and 3C, and close-up in FIG. 5A, the neck portion 1086 of the drive body 1052 can be connected to a proximal end of the body portion 1072. The neck portion 1086 can have an outer diameter smaller than the outer diameter of the body portion 1072 (e.g., a minor diameter surface). The collar 1088 can be connected to a proximal end of the neck portion 1086. The collar 1088 can have an outer diameter greater than the outer diameter of the neck portion 1086 and less than an inner diameter of the force-limiting spring 1054.

The collar 1088 can include the drive surface 1090A at a distal end surface of the collar 1088 and the second distal spring seat 1091 at a proximal end of the collar 1088, or a proximal end of the drive body 1052. As such, the drive surface 1090A can be fixedly connected to or integrally molded to a proximal end of the neck portion 1086. Although the neck portion 1086 and associated flanges, such as drive surface 1090A and the second distal spring seat 1091 are shown and described as being located or connected to a proximal end of the body portion 1072, they could be located elsewhere on the drive body 1052, such as along a central portion or distal portion of the drive body 1052, such as distal of the distal spring seat 1076.

The passageway 1092 in the drive body 1052 (FIG. 3B, 3C) can be shaped to accept the drive shaft 1026. The passageway 1092 can be a cylindrical or non-cylindrical aperture extending through the cylindrical portion 1080, the anchor portion 1074, the body portion 1072, the window portion 1082, the neck portion 1086, and the collar 1088.

The drive shaft 1026 can extend through the passageway 1092 (FIG. 3B) of the drive body 1052 such that the drive body 1052 can be positioned around at least a portion of the drive shaft 1026. The force-limiting spring 1054 can be positioned on the body portion 1072 and over the window portion 1082 of the drive body 1052. A distal end of the force-limiting spring 1054 can contact the distal spring seat 1076. The clip 1056 can be positioned on the window portion 1082 of the drive body 1052 and can connect to drive shaft 1026 at the first vertical slot 1070A and the second vertical slot 1070B. Examples of clips and windows are described further herein, and for example, in FIGS. 4A, 4B, 4C, 5A, 5B, 6A and 6B.

As shown in FIGS. 3A and 3B, and with support for some features shown close-up in FIGS. 5A and 5B, a proximal end of the force-limiting spring 1054 can contact a distal end surface of the clip 1056. As such, the force-limiting spring 1054 can be positioned on the drive body 1052 between the distal spring seat 1076 of anchor portion 1074 and the clip 1056. In this arrangement, the clip 1056 is fixed to the drive shaft 1026 but can be longitudinally movable with respect to the drive body 1052 within and along window portion 1082 (FIGS. 4A, 4B, 4C) when a preload on the force-limiting spring 1054 is exceeded by the force applied to the lever 1024. As shown close-up in FIG. 5B, a clip support surface 1081 of the body portion 1072 can be adjacent a proximal end of the window portion 1082, and a distal support surface 1083 of the body portion 1072 can be adjacent a distal end of the window portion 1082. In some examples, the clip support surface 1081 and the distal support surface 1083 can function as longitudinal stops for the clip 1056 and impose the preload on the force-limiting spring 1054. In an example, the preload can be in a range between 50-150 Newtons. In a possibly more preferred examples, the preload can be in a range between 70-90 Newtons, or 135-155 Newtons, depending on the design. Unlike conventional clips, the clip 1056 can be configured to support such high preloads in combination with features of the clip 1056 that couple the clip 1056 to the drive body 1052 and the drive shaft 1026. One of the benefits of such ranges in combination with the forceps 1000 design, including the clip design 1056, is that such preloads can provide adequate jaw 1012 sealing pressure on a tissue, without requiring an excessive input Force F1 to actuate lever 1024. Furthermore, a single actuating jaw can deliver roughly twice the sealing pressure at the jaws 1012 than a dual-actuating jaw, given the same preload on the force-limiting spring 1054.

To cause driving of the jaws 1012 between the open and closed positions shown in FIGS. 1A and 1B, the lever 1024 is moved proximally or distally which moves the drive body 1052 proximally or distally. The drive link 1046 can be operably coupled to the housing 1014 and the drive body 1052 such that the drive link 1046 is configured to transfer a force received at the lever 1024 into a linear motion of the drive body 1052 and the drive shaft 1026 relative to the housing 1014. For example, the drive link 1046 can be connected to the drive body 1052 at the neck portion 1086. The legs 1046B of drive link 1046, shown in FIG. 3C, can fit around the neck portion 1086. When the lever 1024 is moved proximally, the drive link 1046 can contact and push against the drive surface 1090A of the collar 1088. The location of the drive surface 1090A is shown generally in the cross-sectional view of FIGS. 3B and 3C and close-up in FIG. 5B. In contrast, when the lever 1024 is moved distally, the drive link 1046 can move distally, contacting and pushing against a proximal end surface 1090B of body portion 1072 of drive body 1052, also shown in close-up of FIG. 5B.

During a surgical procedure, carbon dioxide or other gas may be used for insufflation, which introduces a pressure differential between the body cavity and the external environment. As shown in FIGS. 3A-3E, to prevent leakage, the O-ring 1058 can create a seal between the drive shaft 1026 and the outer hub 1060 so that the pressure differential between the body cavity in which the distal portion of forceps 1000 is positioned and the external environment in which the proximal portion of forceps 1000 is located, is maintained. In some examples, the O-ring 1058 can be positioned adjacent and distal to the cylindrical portion 1080.

The sleeve 1061 or the outer shaft 1028 can include the flange 1094 at a proximal end of the sleeve 1061 or the outer shaft 1028. In the example shown, the sleeve 1061 includes the flange 1094. In some examples, the flange 1094 can be welded to, or formed in, the sleeve 1061 or the outer shaft 1028. The flange 1094 can fit within the groove 1096 of outer hub 1060. The flange 1094 can improve the ability to affix the sleeve 1061 or outer shaft 1028 to the outer hub 1060. For example, the flange 1094 can fit in the groove 1096 in the outer hub 1060. The groove 1096 can form a ring in the interior surface 1098 of the outer hub 1060. In some examples, the outer hub 1060 can be molded to the outer shaft 1028. In another example, the outer hub 1060 can be overmolded on to the sleeve 1061. In such a case, there is not necessarily a groove 1096, but the shape of the outer hub 1060 that accepts the flange 1094 can be formed by the overmolding of the outer hub 1060 onto the flange 1094.

To rotationally fix the outer hub 1060 to the drive body 1052, as shown in FIGS. 3D and 3E, the anti-rotation key 1100 can include a ridge that extends out of the interior surface 1098 of the outer hub 1060 into a channel of the outer hub 1060. For example, the anti-rotation key 1100 can be sized to fit within the rotational keying slot 1078 of the anchor portion 1074. The rotational keying slot 1078 can accepts the anti-rotation key 1100, which can be positioned within the rotational keying slot 1078 such that the rotational keying slot 1078 can be linearly translated, or longitudinally moved, along the anti-rotation key 1100. These features are shown in further detail in FIGS. 9A and 9B.

The flange 1094 and the groove 1096 or other formation can connect and lock the outer shaft 1028 to the outer hub 1060. The anti-rotation key 1100 and rotational keying slot 1078 can connect and rotationally lock the outer hub 1060 and the drive body 1052. Also, the drive shaft 1026 can be rotationally locked to the drive body 1052 by the clip 1056. Thus, rotating rotational actuator 1030 (e.g., applying rotational R1 as shown in FIG. 1B) rotates the outer hub 1060, which rotates both the outer shaft 1028 and the drive shaft 1026. The connection between the outer hub 1060, the drive body 1052 and the rotational actuator 1030 is shown and described in further detail with reference to FIGS. 8A, 8B, 9A and 9B.

As shown in FIG. 3C, to improve stabilization of the drive shaft 1026 while allowing one or both of rotation and longitudinal motion, the first housing portion 1016 can include the stabilizing flange 1021 including the recess or the opening 1021A through which a proximal end of the drive shaft 1026 can extend into or through.

To provide articulation of the lever 1024, the lever 1024 can be operably coupled to the housing 1014 via the first pin 1038. The lever 1024 can be movable about the first pin 1038 by a pivoting motion. In the example, the first pin 1038 is retained in the housing 1014. In other examples, the first pin 1038 may be retained by the lever 1024 or may be part of the lever 1024. As shown in FIG. 3A, the lever 1024 can be biased to a default position by lever return spring 1040. In the example, lever return spring 1040 can be constrained between the housing 1014 and the lever 1024. In some examples, the lever return spring 1040 can be provided as any suitable type of biasing element, such as a helical spring, an elastomeric component, an elastomeric band, or an elastomeric block arranged to bias the lever to a default position. Such a biasing element can be strained, for example by compression, extension, torsion or deflection, and elastically return to its original form, or substantially original form.

As a general overview, to transmit an input motion (e.g., input force F1) received at the lever 1024, a first end of the coupling link 1042 can be connected to the lever 1024 via the second pin 1044. A second end of the coupling link 1042 can be connected to a first end of the drive link 1046 via the third pin 1048. As such, the coupling link 1042 can connect the lever 1024 to the drive link 1046. A second end of the drive link 1046 can be connected to the housing 1014 via the fourth pin 1050. The drive link 1046 can be formed as a yoke. For example, as shown in FIG. 3C, the drive link 1046 can include a base 1046A between the first end and the second end of the drive link 1046. A pair of spaced apart legs 1046B can extend from the base 1046A of drive link 1046 such that the ends of the legs 1046B form the second end of drive link 1046.

The illustrative forceps 1000 includes a drive shaft motion transfer assembly 1051 coupled to the housing 1014. The drive shaft motion transfer assembly 1051 can include the drive body 1052 which functions to transmit an input force F1 from the lever 1024 to the drive shaft 1026 to retract or extend the drive shaft 1026 (e.g., to open or close jaws 1012).

In addition to transmitting the input force F1 from the lever 1024 to the drive shaft 1026, in some examples, and as shown in the example forceps 1000, the drive shaft motion transfer assembly 1051, including the drive body 1052 can also transmit a rotational motion from the rotational actuator 1030, through the outer hub 1060, to both the drive shaft 1026 and the outer shaft 1028. However, not all examples of the drive body 1052 require that the drive body 1052 transmit both a longitudinal motion and a rotational motion to the drive shaft 1026. In some examples, the drive body 1052 may only be configured to transmit one or the other of a longitudinal motion and a rotational motion through the drive body 1052 to the drive shaft 1026. For example, some medical devices may employ the extension or retraction features of forceps 1000 but without rotation; and vice versa, other medical devices may employ the rotation features without the extension or retraction features.

In the illustrative drive shaft motion transfer assembly 1051, the drive body 1052 can be positioned around the drive shaft 1026. The drive shaft 1026 can extend through a passageway 1092 in the drive body 1052 (FIG. 3B, 3C). In some examples, the passageway 1092 may be formed as a center bore, though in some examples, the passageway 1092 does not need to be central and/or does not need to be provided as a circular bore. In other examples, the passageway 1092 can be square, polygonal, irregular, or include a notch. In some examples, the passageway 1092 can include a channel. In some examples the passageway 1092 may not surround the drive shaft 1026.

The drive body 1052 can be located distal with respect to the lever 1024 and can be coupled to the lever 1024. In the example, the drive body 1052 is coupled to the lever 1024 indirectly through a series of linkages. The drive body 1052 can be connected to and receive an input force F1 from the lever 1024 via the drive link 1046 to retract or extend the drive shaft 1026 relative to the housing 1014 and the outer shaft 1028 (thereby closing or opening the jaws 1012). The drive body 1052 can be positioned within the yoke formed by the drive link 1046 to receive the input from the drive link 1046.

The drive shaft motion transfer assembly 1051 can include the force-limiting spring 1054 and the clip 1056. The force-limiting spring 1054 can be positioned around the drive body 1052. The clip 1056 can be positioned on the drive body 1052 adjacent and end of the force-limiting spring 1054. The clip 1056 can be fixed to the drive shaft 1026. In some examples, the force-limiting spring 1054 can be any suitable type of biasing element such as an elastomeric component, an elastomeric band, or an elastomeric block that can be elastically deformed and return to its original state, or substantially original state. In some examples, clip 1056 may be inserted onto the drive shaft 1026 via one or more slots (such as vertical slots 1070A and 1070B). In some examples the clip can be flat, while in other examples, the clip may be non-planar or have irregular, non-flat surfaces.

In some examples, the drive shaft motion transfer assembly 1051 can include the outer hub 1060 which can be connected to the drive body 1052. The outer hub 1060 can include an interior surface 1098 within which the drive body 1052, the force-limiting spring 1054, and the clip 1056 (FIG. 3A, FIG. 3C) can translate longitudinally together.

The rotational actuator 1030 can be positioned around and connected to the outer hub 1060. The rotational actuator 1030 can be rotationally constrained to the outer hub 1060 and axially constrained to the outer hub 1060. The rotational actuator 1030 can also be axially constrained with respect to the housing 1014. The nose 1062 can be connected to a distal end of the outer hub 1060, for example, by a snap fit, adhesive or threaded connection. The drive shaft 1026 and the outer shaft 1028 can extend through and out of nose 1062. In some examples the rotational actuator 1030 and/or the nose 1062 can be omitted and the outer hub 1060 can act as the rotational actuator 1030 and/or the nose 1062 to receive a rotation input directly from a user. In some examples, instead of the nose 1062 being connected to a distal end of the outer hub 1060, the nose 1062 can be connected directly to the rotational actuator 1030, for example, by a snap fit, adhesive or threaded connection.

In the example of FIG. 3A, axial retention of the rotational actuator 1030 relative to the housing 1014 can be provided by axially constraining the rotational actuator 1030 between the housing 1014 and the nose 1062. A connection between a first snap fit connector 1060C on the outer hub 1060 and a second snap fit connector 1062C on the nose 1062 can constrain the rotational actuator 1030 from moving distally.

The first and second snap fit connectors are shown merely as an example, any type of snap fit connectors, or otherwise, may be provided. In this arrangement, the outer hub 1060 can be axially constrained with respect to the housing 1014 by a proximal housing flange 1060A and a distal flange 1060B of the outer hub 1060, which can be captured by surfaces of the housing 1014 that interface with the proximal housing flange 1060A and the distal flange 1060B. Furthermore, since the nose 1062 is axially constrained to the outer hub 1060, the rotational actuator 1030 can also be axially constrained to the outer hub 1060, the nose 1062 and the housing 1014 by being captured between the nose 1062 and the housing 1014. In other words, the nose 1062 engages the outer hub 1060 in an axial direction to provide axial retention of both the nose 1062 as well as the rotational actuator 1030.

Figure 4A:
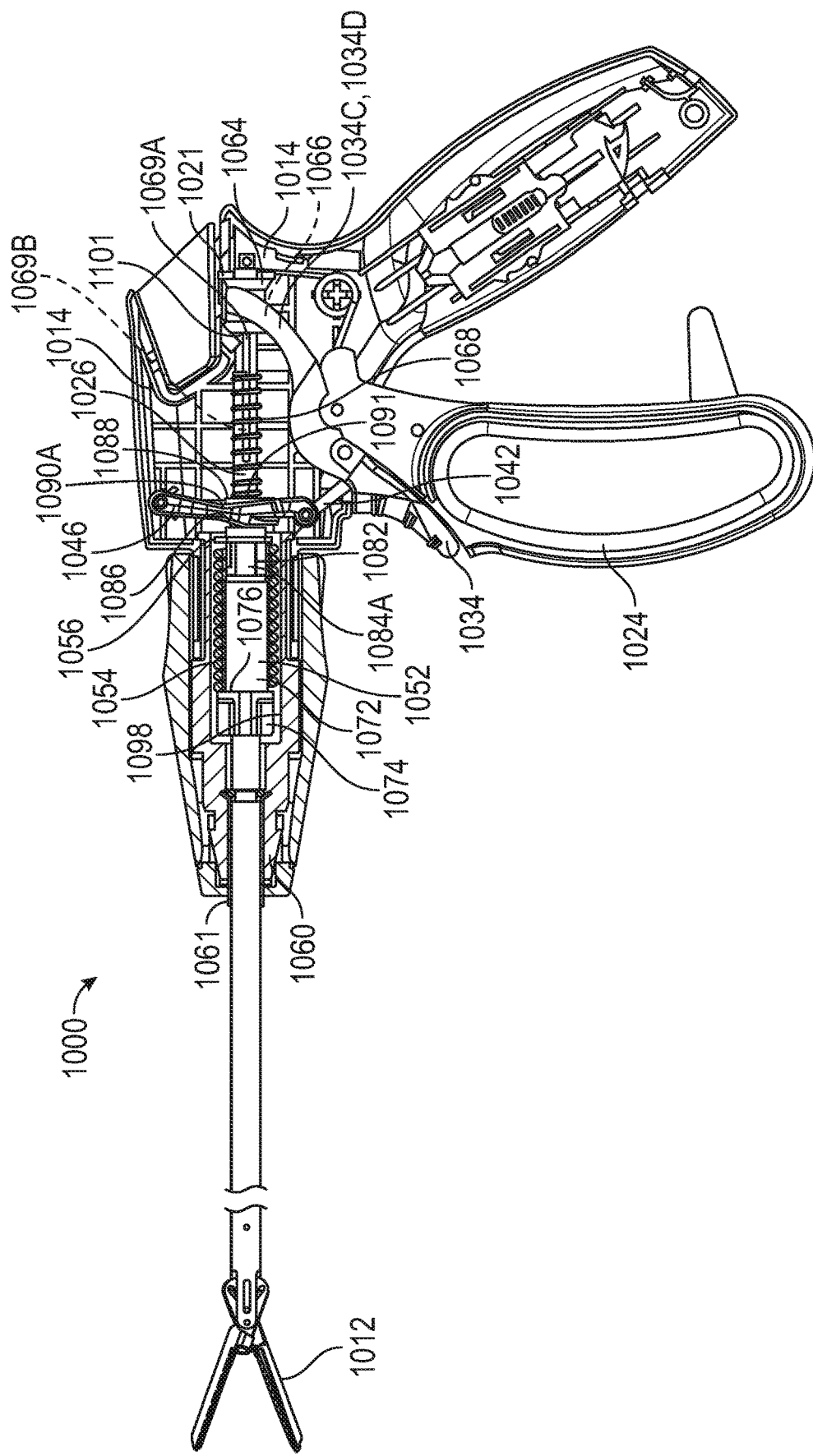
FIG. 4A illustrates a partial cross-sectional view of the forceps of FIG. 1A showing a lever in a distal position (e.g., unactuated position), in accordance with at least one example.
Figure 4B:
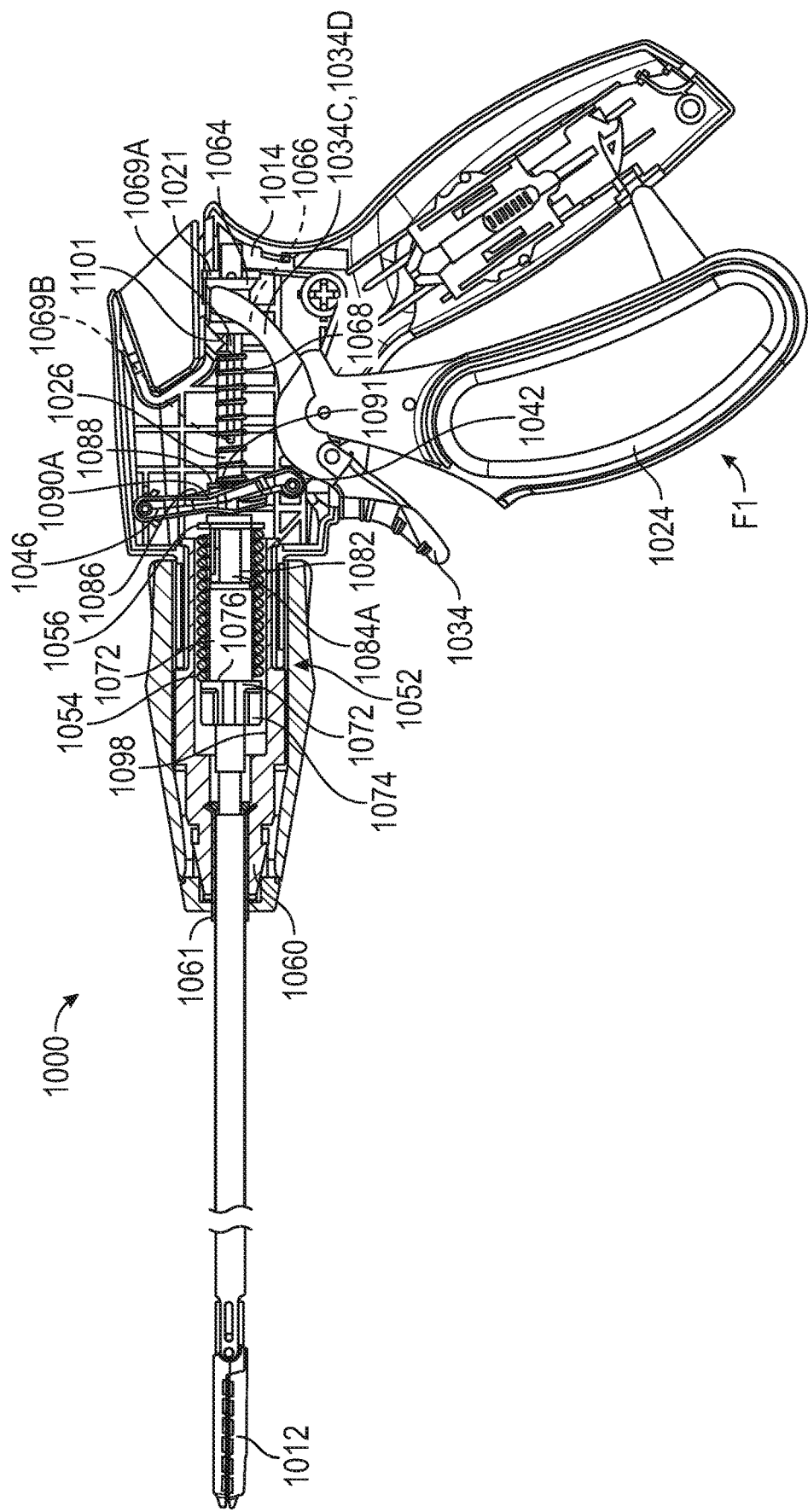
FIG. 4B illustrates a partial cross-sectional view of the forceps of FIG. 1A showing the lever moved proximally (e.g., an actuated position), in accordance with at least one example.
Figure 4C:
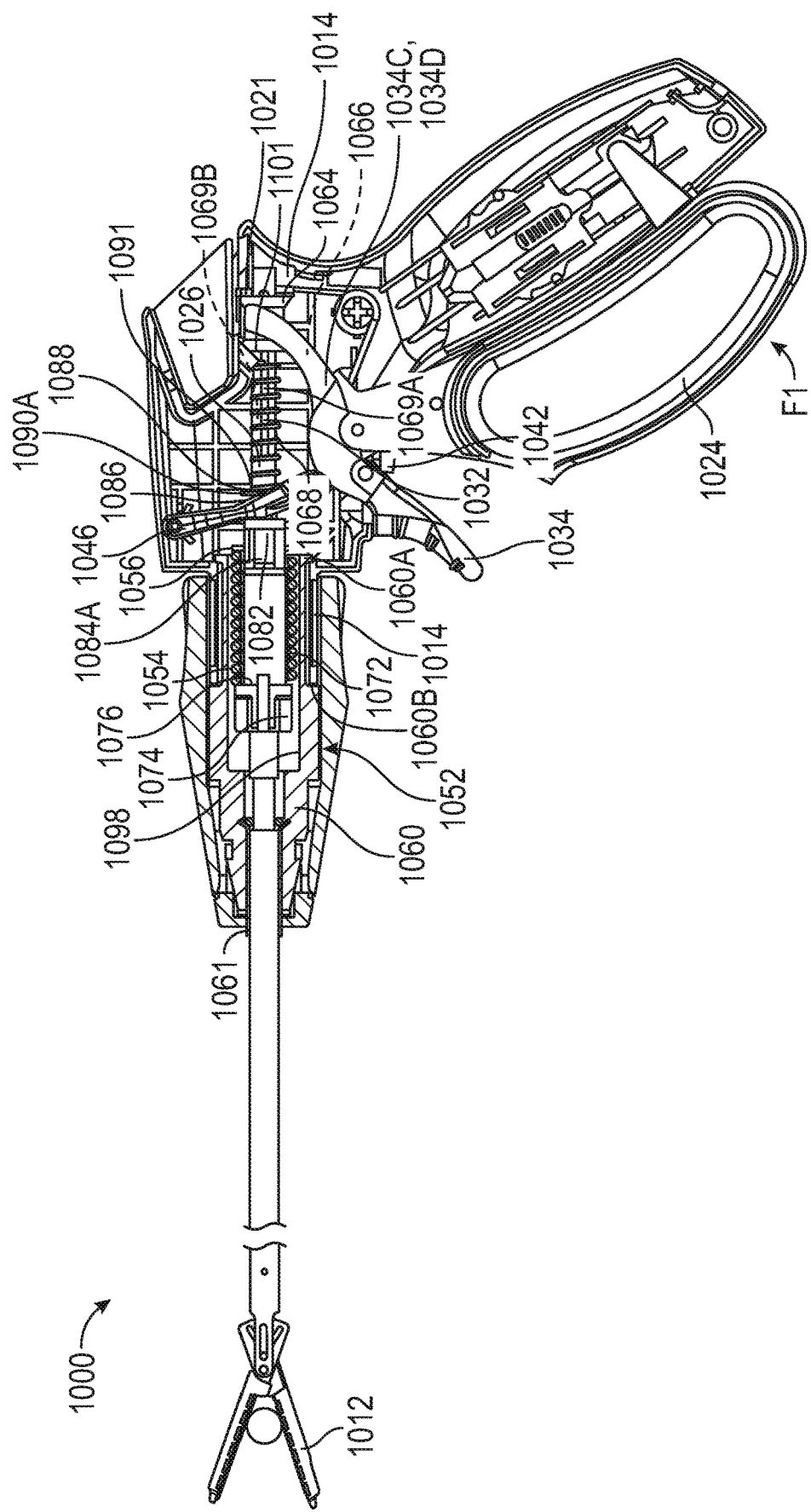
FIG. 4C illustrates a partial cross-sectional view of the forceps of FIG. 1A showing the lever moved further proximally (e.g., a force limiting state, an over-travel position, and in this illustration, a further actuated position than FIG. 4B), in accordance with at least one example.

FIG. 4A illustrates a partial cross-sectional view of the forceps 1000 of FIG. 1A showing the lever 1024 in a distal position (e.g., an unactuated position), in accordance with at least one example. FIG. 4B illustrates a partial cross-sectional view of the forceps 1000 of FIG. 1A showing the lever 1024 being moved proximally (e.g., an actuated position, one of a plurality of actuated positions or user positions), in accordance with at least one example. FIG. 4C illustrates a partial cross-sectional view of the forceps 1000 of FIG. 1A showing the lever 1024 moved further proximally (e.g., into a further actuated position, which in some examples can be a fully actuated position, and in this case, into a force limiting or over-travel state), in accordance with at least one example. Note that a force limiting state is a position of the drive body 1052 that occurs when a force applied to the lever 1024 and transferred to the drive body 1052 exceeds a predetermined force that is based on a preload of the force-limiting spring 1054. Force limiting can occur in other actuated positions whenever the predetermined force is exceeded.

FIG. 4A, FIG. 4B, and FIG. 4C will be discussed together and provide a general illustration of how the drive body 1052, the force-limiting spring 1054, and the clip 1056 can function on the drive shaft 1026 in response to the lever 1024 providing an input to a linkage between the lever 1024 and the drive body 1052. The components of the forceps 1000 shown in FIG. 4A, FIG. 4B, and FIG. 4C include the housing 1014 having stabilizing flange 1021, the lever 1024, the drive shaft 1026, the trigger 1034, the coupling link 1042, the drive link 1046, the drive body 1052, the force-limiting spring 1054, the clip 1056, the outer hub 1060, a spool 1064, the cross pin 1066, and the trigger return spring 1068. The drive shaft 1026 can include the first horizontal slot 1069A, the second horizontal slot 1069B, the first vertical slot 1070A, and the second vertical slot 1070B (hidden here, but viewable in FIG. 3C). The drive body 1052 includes the body portion 1072, the anchor portion 1074 (including distal spring seat 1076), the window portion 1082 (including the first window 1084A and the second window 1084B), the neck portion 1086, and the collar 1088 (including the drive surface 1090A and the second distal spring seat 1091, also shown in FIG. 3C, and close-up in FIG. 5A). The outer hub 1060 includes the interior surface 1098. The spool 1064 can include a proximal trigger return spring seat 1101. The spool 1064 is shown as one example of a motion transfer body designed to transmit motion received from an actuator to a shaft (e.g., received from trigger 1034 and transmitted to blade shaft 1032). In other examples a motion transfer body within this disclosure need not be spool-shaped, such as in examples where the spool 1064 does not need to be rotatable.

As shown in FIG. 4A, when the lever 1024 is in a distal position (e.g., default position, open position of jaws 1012), the drive body 1052 is positioned within the channel formed by interior surface 1098 of outer hub 1060. Most of the body portion 1072 of the drive body 1052 is within the channel of the outer hub 1060. The drive shaft 1026 is in a first position with respect to housing 1014 as it is not being pulled proximally (e.g., unactuated position, non-retracted position) by clip 1056 and is within the opening in the stabilizing flange 1021. As a result, the jaws 1012 are in an open position as shown in FIG. 1A.

As shown in FIG. 4B, when the lever 1024 is being moved proximally, the lever 1024 pulls the bottom end of the drive link 1046 in a proximal direction with respect to housing 1014 via the coupling link 1042. The drive link 1046 is connected to the drive body 1052 at the neck portion 1086 and pushes on the drive surface 1090A of the collar 1088, causing the drive body 1052 to move in a proximal direction longitudinally with respect to the housing 1014. As a result, a greater portion of the body portion 1072, including the window portion 1082, of the drive body 1052 moves out the channel of the outer hub 1060. When the drive body 1052 is pulled proximally, the force-limiting spring 1054 and the clip 1056 move along with the drive body 1052 in the same positions with respect to the drive body 1052.

In other words, the distal spring seat 1076 drives the force-limiting spring 1054, which drives the clip 1056, along with the drive body 1052. When the drive force supplied by the drive link 1046 is less than the preload force in the force-limiting spring 1054, the force-limiting spring 1054 acts like a rigid body and the ends of the force-limiting spring 1054 move together. As such, the drive body 1052 moves proximally with respect to the housing 1014 and the clip 1056 moves proximally with respect to the housing 1014. Because the clip 1056 is longitudinally locked to the drive shaft 1026 at the first vertical slot 1070A and the second vertical slot 1070B, the drive shaft 1026 also moves proximally with respect to the housing 1014. As the drive shaft 1026 moves proximally (e.g., is retracted), the end effector 1002 becomes actuated. In this example, actuating the end effector 1002 includes the jaws 1012 beginning to close.

In other words, in the situation of FIG. 4B, the lever 1024 may be closed due to user input to close jaws 1012. Movement of the lever 1024 causes movement of drive body 1052. Closing lever 1024 causes the coupling link 1042 to pull drive link 1046 proximally with respect to housing 1014, which causes longitudinal translation of drive body 1052 in the proximal direction. Moving the drive body 1052 proximally causes longitudinal translation of the drive shaft 1026 in the proximal direction because the drive body 1052 and the drive shaft 1026 are connected via the clip 1056. As a result of the movement of the drive shaft 1026, a mechanism on the jaws 1012 is actuated, closing the jaws 1012. As shown in the illustrative example, while the drive link 1046 drives the drive body 1052 longitudinally, the drive body 1052 can still be free to rotate inside the yoke of the drive link 1046 and can rotate relative to the drive link 1046. However, in some examples, the rotation aspect may be omitted.

In the illustrative example, at any time during use, regardless of whether the jaws 1012 are opened or closed, the jaws 1012 can be rotated. For example, rotation of the rotational actuator 1030 rotates the outer hub 1060, which beneficially transfers rotational motion to rotate the outer shaft 1028 and the drive body 1052. Because drive body 1052 is locked (e.g., constrained) to the drive shaft 1026 via the clip 1056, the drive shaft 1026 can also rotate with the outer shaft 1028. Thus, the outer shaft 1028 and the drive shaft 1026 can be rotationally locked together (e.g., rotationally constrained) at a proximal end of forceps 1000, and as is described further herein, the outer shaft 1028 and the drive shaft 1026 can also be rotationally locked or constrained together at a distal end of the forceps 1000 proximate the jaws 1012.

Further, first horizontal slot 1069A and second horizontal slot 1069B in drive shaft 1026 can engage and rotate cross pin 1066 when the drive shaft 1026 is rotated, to rotate blade shaft 1032 and spool 1064. Thus, the drive shaft 1026 and blade assembly (1032, 1032A) can be rotationally constrained (e.g., fixed, locked together) at a proximal end of forceps 1000 via cross pin 1066 (FIG. 2, FIG. 4A). In other words, the blade assembly (1032, 1032A) can be rotationally constrained to the drive shaft 1026 at a longitudinal location along the longitudinal axis A1 (FIG. 1B) that is proximal of the jaws 1012 and proximal of the drive body 1052.

If actuation is complete, to return the jaws 1012 to the unactuated state of FIG. 4A, the lever return spring 1040 can act on the lever 1024 to return (e.g., bias) the lever 1024 to the default position (e.g., distal position). Since the lever 1024 is coupled to the drive shaft 1026 by a series of linkages, the lever return spring 1040 also returns the drive shaft 1026 and thereby the jaws 1012 to a default position, which in the present example is an open position. As shown in the condition of FIG. 4C, it is possible that jaws 1012 may become stuck or caught on an anatomical feature or another medical device in the patient when the lever 1024 is being moved proximally. In such a situation, the jaws 1012 may not be able to close completely. However, the drive motion transfer assembly 1051 of forceps 1000 includes a force limiting feature that prevents the drive shaft 1026 from being retracted to the point where the jaws 1012 become damaged by the additional input force F1 from the user being transmitted to the jaws 1012. The forceps 1000 can be capable of achieving a force limiting state (e.g., an overtravel state) in instances where the lever 1024 is being moved proximally and the jaws 1012 get stuck in an open or partially open position and the user continues to apply a force to the lever 1024.

To prevent damage to the jaws 1012, the force-limiting spring 1054 can be configured to absorb excess force applied to the lever 1024 instead of transferring the excess force to the jaws 1012. For example, the force-limiting spring 1054 can extend from a first end portion to a second end portion and can be in a preloaded state between the distal spring seat 1076 and a distal end surface 1105 of the clip 1056. The force-limiting spring 1054 can push the clip 1056 in a proximal direction such that the clip 1056 contacts and is supported by a clip support surface (e.g., proximal support surface 1081, FIG. 5B) of the body portion 1072 adjacent a proximal end of the window portion 1082. The clip support surface (1081, FIG. 5B) can function as a proximal stop for the clip 1056. With the force-limiting spring 1054 in compression, the distal spring seat 1076 can be configured to receive a first spring force from the distal end portion of the force-limiting spring 1054, and the clip 1056 can be configured to receive a second spring force from the proximal end portion of the force-limiting spring 1054. The drive body 1052 can include the clip support surface 1081 configured to transmit the first force to the second surface (e.g., proximal end surface 1103) of the clip 1056 when the force-limiting spring 1054, under a load, such as a preload, drives the clip 1056 against the clip support surface 1081.

With continued reference to FIG. 4C, in an example of force limiting, the lever 1024 is moved to a proximal position by the user, exerting force on the drive link 1046 and pulling the bottom end of drive link 1046 further in a proximal direction, although the jaws 1012 are blocked from closing further. Consequently, the drive link 1046 exerts more force on the drive surface 1090A of the collar 1088, moving the drive body 1052 further proximally with respect to housing 1014 and the drive body 1052 moves farther proximally out of the interior surface 1098 that forms a passageway 1098A (FIG. 3C) of the outer hub 1060. The outer hub 1060 can be constrained from axial movement with respect to the housing 1014 by proximal housing flange 1060A and distal flange 1060B of the outer hub 1060 which can be captured by a portion of housing 1014. As the drive body 1052 moves proximally, the distal spring seat 1076 of the anchor portion 1074 of the drive body 1052 pushes on a distal end of the force-limiting spring 1054. However, because the jaws 1012 are unable to close further, the drive shaft 1026 cannot move proximally along with the drive body 1052. Further, because the clip 1056 is locked to drive shaft 1026, the clip 1056 cannot move proximally with respect to housing 1014 either. Thus, the drive body 1052 moves proximally relative to the clip 1056 and the drive shaft 1026 by sliding (e.g., linear motion, longitudinal motion or translating) proximally relative to the clip 1056.

The clip 1056, by remaining fixed with respect to the drive shaft 1026, effectively moves distally relative to the drive body 1052 within the first window 1084A and the second window 1084B of the window portion 1082. As such, the force-limiting spring 1054 becomes more compressed between the distal spring seat 1076 and the distal end surface of the clip 1056 when the force exerted on the drive link 1046 is greater than a preload of the force-limiting spring 1054. The user can feel this force limiting feature as an increase in force on the lever 1024 due to the additional compression of the force-limiting spring 1054 over the preloaded state, however, the lever 1024, which is no longer transferring motion to the drive shaft, is still movable.

In other words, the lever 1024 can be fully moved into a proximal position, moving the drive body 1052 proximally in the housing 1014 as far as the drive shaft 1026 will go. At the same time, the jaws 1012 can become locked in an open position (e.g., caught on something), preventing the drive shaft 1026 from moving even though the lever 1024 is being moved proximally. Because the drive shaft 1026 cannot move proximally in the housing 1014, the clip 1056 cannot move proximally with respect to the housing 1014. However, because the clip 1056 can slide within the window portion 1082, the drive body 1052 is able to move (e.g., slide, translate) proximally with respect to the clip 1056, changing the position of the clip 1056 within the window portion 1082. As the drive body 1052 moves with respect to the clip 1056, the force-limiting spring 1054 compresses and absorbs the force exerted on the lever 1024. Because moving the drive shaft 1026 causes the jaws 1012 to close, the ability to prevent the drive shaft 1026 from moving when the jaws 1012 are unable to close prevents the jaws 1012 from becoming damaged when a user is unaware of the jaws 1012 being stuck open and the user continues to pull the lever 1024 proximally to close the jaws 1012.

FIG. 5A is an isometric view of an example drive shaft motion transfer assembly 1051 that can be used in the forceps 1000 of FIG. 1A, including the drive body 1052, the force-limiting spring 1054 shown in cross-section, the clip 1056 and the drive shaft 1026. FIG. 5B is an exploded view of the drive body 1052, the clip 1056, the force-limiting spring 1054 and the drive shaft 1026. FIGS. 5A and 5B are discussed together.

The motion transfer assembly 1051 serves to transfer a force input F1 (FIG. 1B) applied by a user at lever 1024 and/or a rotational input R1 applied by a user at rotational actuator 1030, to the end effector 1002 (FIG. 1B).

The motion transfer assembly 1051 of the example of FIGS. 5A and 5B is described as follows. The drive shaft 1026 can include the first vertical slot 1070A and the second vertical slot 1070B. The drive body 1052 can include the body portion 1072, the anchor portion 1074 (including the distal spring seat 1076), and the window portion 1082 (including the first window 1084A and the second window 1084B, see FIG. 5B), surfaces to interface with the drive link 1046, including the collar 1088, the neck portion 1086 and the distal collar 1089 (e.g. a distal surface, a proximally-facing distal face). The clip 1056 can include a clip body 1102 having a proximal end surface 1103 and a distal end surface 1105 (e.g., a proximal spring seat 1104), The clip 1056 can include a clip body 1102, a clip slot 1106, one or more of a first clip notch 1108A, and one or more of a second clip notch 1108B. The drive shaft 1026 can include one or more of a first vertical slot 1070A, a second vertical slot 1070B, and one or more of a first tab 1026A and a second tab 1026B. The first and second vertical slots 1070A, 1070B can be provided as an opening/aperture or as a deformation with or without an opening through the drive shaft 1026. The first tab 1026A and/or the second tab 1026B can be cantilevered tabs. The drive shaft 1026, drive body 1052, force-limiting spring 1054, and the clip 1056 can have the same structure and function as described with respect to FIGS. 1A-4C.

The drive body 1052 can have the clip 1056 positioned on the drive body 1052 and connected to the drive shaft 1026, which extends through the drive body 1052. The force-limiting spring 1054 can be positioned around the drive body 1052.

The first clip notch 1108A and the second clip notch 1108B can extend into the clip body 1102 at a middle of the clip slot 1106. The first clip notch 1108A can extend into the clip body 1102 from a first side of the clip slot 1106 at a middle of the clip slot 1106, or near a middle of the clip slot 1106, and the second clip notch 1108B can extend into the clip body 1102 from a second side of the clip slot 1106 at the middle of the clip slot 1106, or near the middle of the clip slot 1106. As such, the second clip notch 1108B extends into the clip body 1102 from the clip slot 1106 opposite first the clip notch 1108A.

The drive shaft 1026 can include the first tab 1026A and the second tab 1026B. The first tab 1026A can be cantilevered and can extend horizontally along a first side of the drive shaft 1026 through the vertical slot 1070A on the first side of the drive shaft 1026. The second tab 1026B can be cantilevered and can extend horizontally along a second side of the drive shaft 1026 through the vertical slot 1070B on the second side of the drive shaft 1026.

When the drive body 1052 is on the drive shaft 1026, the clip 1056 can be positioned on window portion 1082 of the drive body 1052. The clip 1056 fits around the drive body 1052 at the window portion 1082 and can be positioned on the drive body 1052 anywhere along a length of the window portion 1082. The clip 1056 can also fit around the drive shaft 1026 at the first vertical slot 1070A and the second vertical slot 1070B such that the clip 1056 fits within the first vertical slot 1070A and the second vertical slot 1070B of the drive shaft 1026. The first tab 1026A and the second tab 1026B can be cantilevered and resilient such that they are pushed inwards when the clip 1056 is placed on the drive shaft 1026, and form a resilient joint (e.g., one or more components is resiliently deformed, substantially resiliently deformed). When the clip 1056 is fully positioned within the first vertical slot 1070A and the second vertical slot 1070B, the cantilevered first tab 1026AA can spring out and can fit within the first the clip notch 1108A, and the cantilevered second tab 1026B can spring out and fits within the second clip notch 1108B. The clip 1056 can move longitudinally within the first window 1084A and the second window 1084B along the entire length of the window portion 1082.

The clip 1056 can be positioned on the drive body 1052 anywhere along the entire length of the window portion 1082 making assembly easy. Further, as a result, the force-limiting spring 1054 is not required to compress to a distal end of the window portion 1082, making the spring 1054 easier to manufacture. The cantilevered tabs 1026A and 1026B can fit within the clip notches 1108A and 1108B to retain the clip 1056 to the drive shaft 1026 and the drive body 1052, longitudinally and rotationally lock the clip 1056 to the drive shaft 1026 (along with the vertical slots 1070A and 1070B), and rotationally lock the clip 1056 to the drive body 1052. The clip 1056 can remain capable of moving longitudinally within the first window 1084A and the second window 1084B along the window portion 1082 of the drive body 1052. Because the clip 1056 does not need to be retained on the drive body 1052 via retaining ribs, the clip 1056 can translate along the entire length of the window portion 1082 without dislodging from, popping off the drive body 1052, or backing out (e.g., separating from the drive body 1052 or the drive shaft 1026 by movement in a direction opposite a direction of insertion during assembly). In the present example, this direction is in a direction perpendicular to, upward and away from the longitudinal axis A1 (FIG. 1B).

The first vertical slot 1070A and the second vertical slot 1070B on the drive shaft 1026 longitudinally and rotationally lock the clip 1056 to the drive shaft 1026. Since the clip 1056 is prevented from backing out of the first vertical slot 1070A, the second vertical slot 1070B, and the window portion 1082, the clip 1056 is rotationally locked to the drive body 1052. However, some instances (e.g., force limiting state), as described herein, the drive body 1052 is still capable of moving longitudinally with respect to the clip 1056 such that the clip 1056 moves longitudinally with respect to drive body 1052 within the first window 1084A and the second window 1084B. As a result, in a force limiting state (FIG. 4C), the drive body 1052 can move longitudinally relative to the drive shaft 1026. The clip 1056 is prevented from backing out or popping off drive body 1052 and the drive shaft 1026, while drive body 1052 moves longitudinally relative to the clip 1056 and the drive shaft 1026.

In this arrangement, the clip 1056 can be fixed to the drive shaft 1026 and slidably coupled to the drive body 1052. The rotational motion can be delivered from the drive body 1052 through the clip 1056 to the drive shaft 1026, and the linear motion can be delivered from the drive body 1052 indirectly through the force-limiting spring 1054 to the clip 1056 and from the clip 1056 to the drive shaft 1026 to translate the drive shaft 1026.

In other words, the clip 1056 can be coupled to the drive body 1052 and the drive shaft 1026 to rotationally fix the drive body 1052 to the drive shaft 1026. The drive body 1052 can be configured to transfer a rotational input received from the rotational actuator 1030 into a rotational motion of the clip 1056, and the clip 1056 can be configured to transfer the rotational motion of the clip 1056 into a rotational motion of the drive shaft 1026.

As shown in FIG. 5B, the input surfaces to receive an input from the drive link 1046 (FIGS. 3A, 3B, 3C) can include the collar 1088 (e.g., first face), the neck portion 1086 (e.g., minor diameter surface) and the distal collar 1089 (e.g., distal face). The collar 1088, the neck portion 1086 and the distal collar 1089 can form a spool portion of the drive body 1052. In some examples, the spool portion can be an axisymmetric spool portion. In some examples, a distal face 1088B of the proximal collar 1088 and a proximal face 1089A of the distal collar 1089 are planar. In some examples, a distal face 1088B of the proximal collar 1088 and a proximal face 1089A of the distal collar 1089 are parallel. In some examples, the spool-like portion of the drive body 1052 (e.g., 1088, 1086 and 1089) allows for rotational displacement of the drive body 1052 relative to the drive link 1046.

Figure 6B:
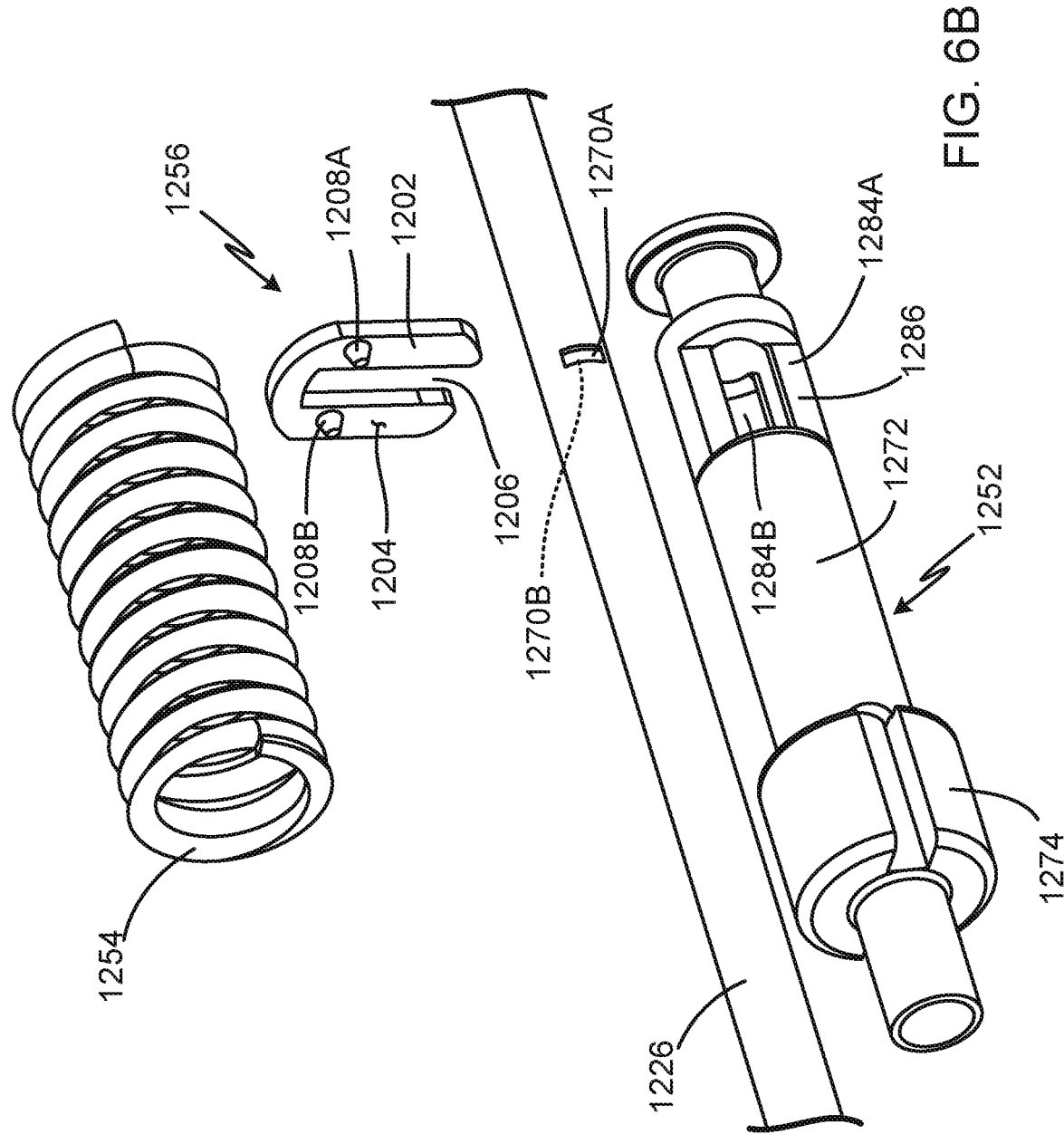
FIG. 6B illustrates an exploded view of the second example of the drive shaft motion transfer assembly of FIG. 6A, in accordance with at least one example.

FIG. 6A illustrates an isometric view of a second example of a motion transfer assembly that can be used in the forceps of FIG. 1A. FIG. 6A includes a drive body 1252, a clip 1256 and a cross-section of a force-limiting spring 1254 on a drive shaft 1226. FIG. 6B is an exploded view of the drive body 1252, the clip 1256, the force-limiting spring 1254 and the drive shaft 1226 of FIG. 6A. FIGS. 6A and 6B are discussed together.

The drive body 1252 includes a body portion 1272, a window portion 1282 (including a first window 1284A, a second window 1284B, and an anchor portion 1274). The clip 1256 includes a clip body 1202, having a proximal end surface 1203 and a distal end surface 1205 (e.g., a proximal spring seat 1204), a clip slot 1206, one or more protrusions such as a first protrusion 1208A, and a second protrusion 1208B. In an example, the first and second protrusions 1208A, 1208B can be provided as a bump, knob, deformation or added material. The drive shaft 1226 includes one or more of a first vertical slot 1270A and a second vertical slot 1270B provided as an opening/aperture or as a deformation with or without an opening through the drive shaft 1226.

The drive body 1252 can have the clip 1256 positioned on the drive body 1252 and connected to the drive shaft 1226, which extends through the drive body 1252. The spring 1254 can be positioned around the drive body 1252.

The drive body 1252 has generally the same structure and function as the drive body 1152 described with respect to FIGS. 1A-5B, including the body portion 1272 and the window portion 1282 having the first window 1284A and the second window 1284B. However, in some examples, the anchor portion 1274 can be cylindrical.

The clip 1256 can have generally the same structure and function as the clip 1156 described with respect to FIGS. 1A-5B, including the clip body 1202, the proximal spring seat 1204 and the clip slot 1206. However, the clip 1256 can include the first protrusion 1208A and the second protrusion 1208B and does not necessarily include clip notches, however a combination of clip notches and protrusions can be provided in some examples. In some examples, the clip 1256 may include only the first protrusion 1208A. The first protrusion 1208A can extend out of a distal end surface of the clip 1256 or can extend from the proximal spring seat 1204. The second protrusion 1208B can extend out of a distal end surface of the clip 1256 (e.g., extend from the proximal spring seat 1204). The first protrusion 1208A and the second protrusion 1208B can make up a pair of protrusions. The clip slot 1206 can extend into the clip body 1202 from a bottom of the clip body 1202 between the first protrusion 1208A and the second protrusion 1208B. In alternate examples, the first protrusion 1208A and the second protrusion 1208B may be positioned anywhere on the clip 1256 relative to the clip slot 1206. The protrusions 1208A, 1208B can be positioned on the clip 1256 such that the protrusions 1208A, 1208B fit inside an inner diameter of the force-limiting spring 1254.

The drive shaft 1226 can be the same as the drive shaft 1026 described with respect to FIGS. 1A-5B.

When the drive body 1252 is on the drive shaft 1226, the clip 1256 is positioned on the window portion 1282 of the drive body 1252. The clip 1256 fits around the drive body 1252 at the window portion 1282 and can be positioned on the drive body 1252 anywhere along an entire length of the window portion 1282. The clip 1256 also fits around the drive shaft 1226 at the first vertical slot 1270A and the second vertical slot 1270B such that the clip 1256 fits within first vertical slot 1270A and second vertical slot 1270B of the drive shaft 1226. When the clip 1256 is positioned within the first vertical slot 1270A and the second vertical slot 1270B, the protrusions 1208A, 1208B can fit inside an inner diameter of the force-limiting spring 1254. In some examples, the protrusions 1208A, 1208B may contact the inner diameter of the force-limiting spring 1254. In alternate examples, protrusions 1208A, 1208B may not contact the inner diameter of the force-limiting spring 1254.

The clip 1256 can be positioned on the drive body 1252 anywhere along the entire length of the window portion 1282 because the window portion 1282 does not necessarily include any sort of retaining ribs, making assembly easier. Further, as a result, the force-limiting spring 1254 is not required to compress to a distal end of the window portion 1282. The protrusions 1208A, 1208B can fit inside an inner diameter of the force-limiting spring 1254 to retain the clip 1256 to the drive shaft 1226 and the drive body 1252. The clip 1256 can remain capable of moving longitudinally within the first window 1284A and the second window 1284B along the body portion 1272 making up the window portion 1282 of the drive body 1252. The clip 1256 can translate along the entire length of the window portion 1282 without dislodging from, popping off or backing out of the drive body 1252 or drive shaft 1226. As a result, the clip 1256 can travel the full distance within the window portion 1282, allowing for good force limiting (e.g., over-travel) abilities.

Figure 7A:
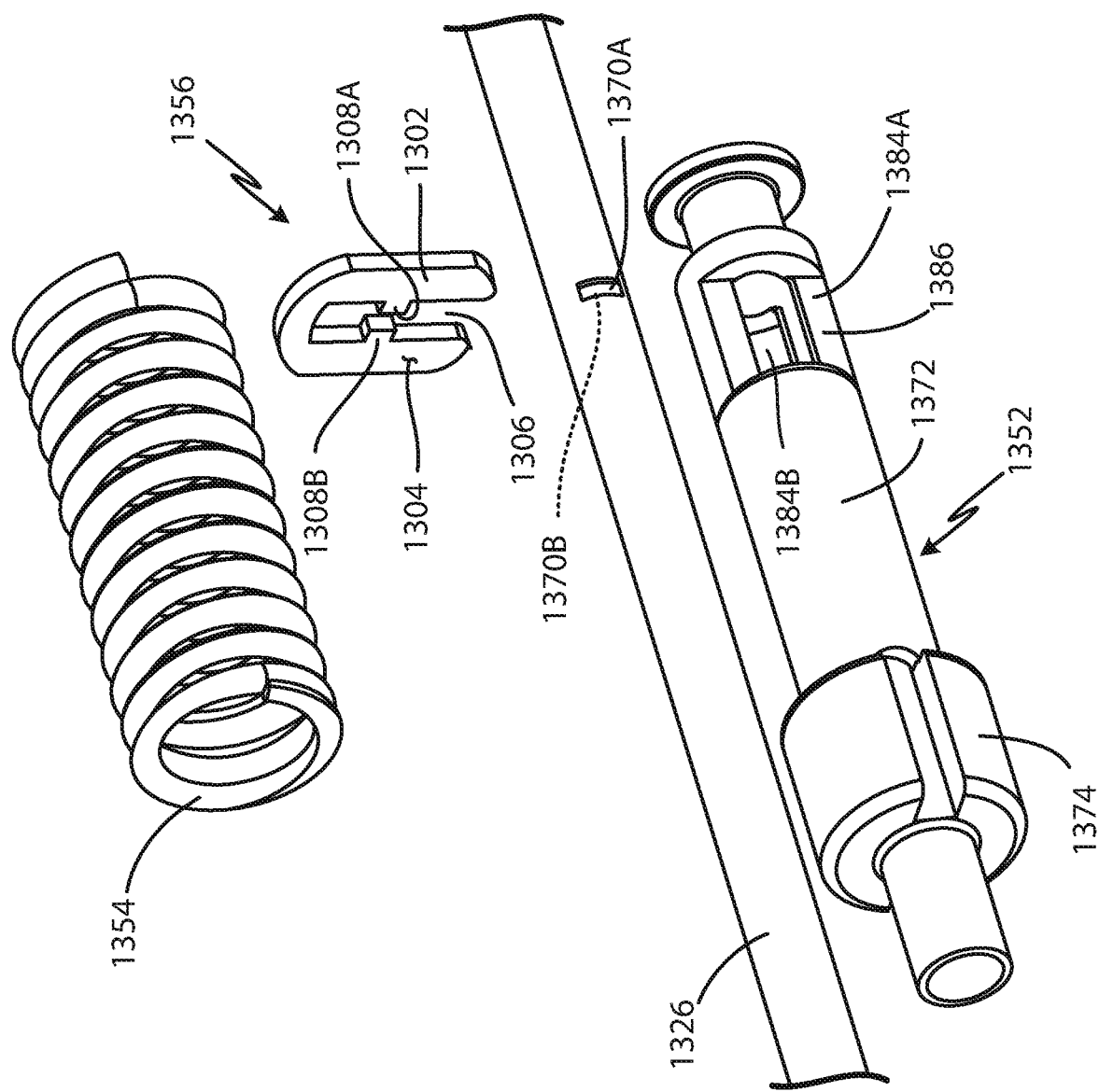
FIG. 7A illustrates an exploded view of a third example of a drive shaft motion transfer assembly that can be used with the forceps of FIG. 1A, in accordance with at least one example.

FIG. 7A illustrates an exploded view of a third example of a drive shaft motion transfer assembly that can be used with the forceps of FIG. 1A The example of FIG. 7A can be the same as the example of FIGS. 5A and 5B with a slightly different configuration for attaching a clip 1356 to the drive shaft 1326. The drive body 1352 has generally the same structure and function as the drive body 1152 described with respect to FIGS. 1A-5B, including the body portion 1372 and the window portion 1382 having the first window 1384A and the second window 1384B.

The clip 1356 can have generally the same structure and function as the clip 1156 described with respect to FIGS. 1A-5B, including the clip body 1302, the proximal spring seat 1304 and the clip slot 1306. However, the clip 1356 can include the first clip slot tab 1308A and the second clip slot tab 1308B. The first clip slot tab 1308A can extend medially from inner slot surface of the clip 1356 that faces a first vertical slot 1370A on the drive shaft 1326. The second clip slot tab 1308B can extend medially from an inner slot surface of the clip 1356. The first and second clip slot tabs 1308A, 1308B can be positioned on the clip 1356 such that the first and second clip slot tabs 1308A, 1308B fit into the first and second vertical slots 1370A, 1370B on the drive shaft 1326, such as by a snap-fit coupling forming a resilient joint. In some examples, the clip 1356 can be elastically deformable such that together the clip 1356 and the drive shaft 1326 form a resilient joint when the first or second clip slot tab 1308A, 1308B is received in the first or second vertical slot 1370A, 1370B. The first or second vertical slot 1370A, 1370B can form either a recess into or opening through the drive shaft 1326.

FIGS. 8A, 8B, 9A and 9B illustrate an example of how the drive shaft 1026 and outer shaft 1028 can be constrained to one another and to the outer hub 1060 and rotational actuator 1030 to transfer this rotational input R1 to the outer shaft 1028 and the drive shaft 1026, and thereby to the end effector 1002 of forceps 1000. FIG. 8A illustrates a side view of a portion of the forceps 1000 of FIG. 1A, in accordance with at least one example. FIG. 8A includes the outer shaft 1028, the outer hub 1060, the housing 1014 and the rotational actuator 1030 (shown in phantom). FIG. 8B is a cross-sectional view of the rotational actuator 1030 and outer hub 1060 of FIG. 8A along line 8A-8A' but with the rotational actuator 1030 shown in solid, in accordance with at least one example.

The outer hub 1060 can be located around at least a portion of the drive body 1052 and the drive shaft 1026. To transfer rotational motion from the outer hub 1060 to the drive shaft 1026, the rotational motion received from the rotational actuator 1030 can be transferred to the outer hub 1060; transferred from the outer hub 1060 to the drive body 1052; transferred from the drive body 1052 to the clip 1056; and transferred from the clip 1056 to the drive shaft 1026. The rotational input R1 received from the rotational actuator 1030 can also be transferred from the outer hub 1060 to the outer shaft 1028 to rotate the outer shaft 1028. In other examples, the clip 1056 can be omitted and/or the passageway 1092 (e.g., bore) in the drive body 1052 can be rotationally keyed to the drive shaft 1026 to transfer the rotational input.

As shown in the combination of FIG. 8A and FIG. 8B, at the proximal portion of the forceps 1000, the rotational actuator 1030 can be constrained to the outer hub 1060 via a keyed interface. For example, the rotational actuator 1030 can include an actuator-hub keyed interface 1033 that is configured to be rotationally constrained to the outer hub 1060 having a complimentary actuator-hub keyed interface 1063. The keyed interface 1033, 1063 can constrain, couple, fix, lock, or limit rotation between the rotational actuator 1030 and the outer hub 1060.

In this arrangement, the outer hub 1060 can be configured to receive a rotational input from the rotational actuator 1030 such that the rotational actuator 1030 and outer hub 1060 can be rotated relative to the housing 1014. In alternate examples, the rotational actuator 1030 can be otherwise attached to the outer hub 1060, such as by integral molding, adhesive, welding, snap-fit, or any other suitable method. In some examples, the rotational actuator 1030 can be omitted and the outer hub 1060 can function as an actuator to receive a rotational input from a user directly. The rotational actuator 1030 is merely shown as one example of a component to receive a rotational input from a user, any suitable rotational input device can be provided.

FIG. 9A illustrates a side view of a portion of the forceps 1000 of FIG. 1A including the housing 1014, the drive shaft 1026, the outer shaft 1028, the drive body 1052 (having a first portion 1052A and a second portion 1052B), the force-limiting spring 1054, the drive link 1046, the outer hub 1060 (shown in phantom), the sleeve 1061, and the jaws 1012 in accordance with at least one example. FIG. 9B is a cross-sectional view of the outer hub 1060 and the drive body 1052 of FIG. 9A along line 9B-9B' with the outer hub 1060 shown in solid, in accordance with at least one example.

To rotationally fix the outer hub 1060 to the drive body 1052, the outer hub 1060 and the drive body 1052 can include a hub-body keyed interface. For example, the outer hub 1060 can include the anti-rotation key 1100, and the drive body 1052 can have a complimentary hub-body keyed interface, such as rotational keying slot 1078. The rotational keying slot 1078 can be located at a second portion 1052B of the drive body 1052 (e.g., distal portion). In this arrangement, the drive body 1052 can be configured to receive a rotational input from the outer hub 1060, supplied to the outer hub 1060 by the rotational actuator 1030 (FIG. 8A, 8B).

The anti-rotation key 1100 can include a ridge that extends out of the interior surface 1098 of the outer hub 1060 into the channel formed by the interior surface 1098. The anti-rotation key 1100 can be sized to fit within the rotational keying slot 1078 of the outer hub 1060. The rotational keying slot 1078 can accept the anti-rotation key 1100 such that the rotational keying slot 1078 can be linearly translated, or otherwise longitudinally moved, along the anti-rotation key 1100 in order to allow retraction and extension of the drive body 1052 with respect to the outer hub 1060 and the housing 1014.

In other words, the anti-rotation key 1100 and rotational keying slot 1078 constrain the outer hub 1060 and the drive body 1052 rotationally, but the drive body 1052 can still move (e.g., slide, translate) along the longitudinal axis A1 relative to the outer hub 1060 when the lever 1024 is actuated by a user applying input force F1 (FIG. 1B). The longitudinal movement of the outer hub 1060 relative to the drive body 1052 allows the drive body 1052 to retract relative to the outer hub 1060 when the lever 1024 is actuated to close the jaws 1012. Such retraction of the drive body 1052 results in retraction of the drive shaft 1026, up until a specified input force F1 is applied to the lever 1024 that exceeds the preload of the force-limiting spring 1054. When the input force F1 exceeds the specified input force, the drive body 1052 can continue to move proximally with respect to the drive shaft 1026 and without retracting the drive shaft 1026. Thereby protecting the end effector 1002 from receiving an excessive force and becoming damaged.

The features described herein provide for improved actuation and overall quality, improved assembly and reduced cost of forceps and other medical devices.

While illustrative examples of a medical device are shown and described in this disclosure with respect to a forceps, the features can be used in other medical devices besides forceps for controlling end effectors used in diagnosis, treatment or surgery. Any representation of a forceps or description thereto is shown primarily for illustrative purposes to disclose features of various examples.

The forceps illustrated in the examples can be an electrosurgical device, however, the forceps may be any type of medical device that facilitates mechanical and/or electrical actuation of one or more end effectors or other elements arranged distal from the handpiece having one or more actuation systems. The actuation systems described, which can extend, retract or rotate one or more shafts to produce this result, can be used to effect actions in other medical devices (e.g., medical instruments).

The directional descriptors described herein are used with their normal and customary use in the art. For example, proximal, distal, lateral, up, down, top and bottom may be used to describe the apparatus with the longitudinal axis arranged parallel to a ground with the device in an upright position. The proximal direction refers to a direction towards the user end of the apparatus, and the distal direction represents a direction towards the patient end of the apparatus.

Relative terms described herein, such as, "about" or "substantially" may be used to indicate a possible variation of ±10% in a stated numeric value, or a manufacturing variation.

As described throughout this disclosure, components and assemblies can be operably connected to each other and interact with one another in a manner that provides improved actuation, a more compact and simpler design, lower cost, and better user satisfaction than traditional medical devices.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A motion transfer assembly for a forceps, the assembly comprising:
   a body having a passageway extending through the body;
   a drive shaft having a slot, the drive shaft extending through the passageway;
   a biasing element having an inner diameter positioned around the body; and
   a clip positioned to apply a compression force to the biasing element, the clip including a protrusion on a face abutting the biasing element,
   wherein:
   the clip is aligned with the slot;
   the protrusion extends out of a distal end surface of the clip and within the inner diameter of the biasing element; and
   the body is configured to move a y relative to the clip and the drive shaft.

2. The assembly of claim 1, wherein the protrusion overlaps with the biasing element in a longitudinal direction to prevent back out of the clip with respect to the drive shaft and the body.

3. The assembly of claim 1, wherein the clip is movable relative to the body along a longitudinal axis of the drive shaft.

4. The assembly of claim 1, wherein the clip includes a plurality of the protrusion.

5. The assembly of claim 1, wherein the body is configured to receive an input force from a drive link, and wherein the input force exceeding a preload of the biasing element causes the body to move linearly.

6. The assembly of claim 1, wherein the clip is slidably coupled to the body along a track in the body.

7. The assembly of claim 1, wherein the clip is slidably coupled to the body, and wherein rotation motion received by the body is delivered from the body through the clip to the drive shaft.

8. The assembly of claim 1, wherein the drive shaft further comprises an opening extending through the drive shaft from an outer diameter to the inner diameter, and wherein the dip extends into the opening.

9. The assembly of claim 1, wherein the face abutting the biasing elements a distal face of the clip.

10. A motion transfer assembly for a forceps, comprising:
    a frame;
    an actuator;
    a body including a passageway extending through the body, the body configured to receive a force from the actuator;
    a drive shaft extending through the passageway and coupled to the frame; and
    a clip coupled to the body and the drive shaft,
    wherein:
    the clip is coupled to one of the body and the drive shaft by a resilient joint between the clip and the drive shaft that deforms during placement of the clip, returns to position when the clip is in place, and prevents lateral dislodgment of the clip; and
    the body is configured to move linearly relative to the clip and the drive shaft.

11. The motion transfer assembly of claim 10, wherein the resilient joint includes a clip notch configured to accept a cantilevered tab of the drive shaft.

12. The motion transfer assembly of claim 10, wherein the clip is elastically deformable and includes a clip slot and a clip slot tab extending medially into the clip slot, and wherein the resilient joint includes a recess or opening in the drive shaft receiving the clip slot tab.

13. The motion transfer assembly of claim 10, wherein the drive shaft includes a longitudinally-extending cantilevered tab, wherein the clip has a clip body including a clip slot and a clip notch extending into the clip slot, wherein the clip notch is configured to receive the cantilevered tab.

14. The motion transfer assembly of claim 13, wherein the cantilevered tab is resiliently deformable to receive the clip body.

15. A motion transfer assembly for a forceps, the assembly comprising:
    a body having a passageway extending through the body;
    a drive shaft extending through the passageway, wherein the drive shaft is slidable with respect to the body;
    a biasing element having an inner diameter, the biasing element positioned around the body; and
    a clip longitudinally and radially constrained to the drive shaft and longitudinally movable relative to the body, the clip positioned to apply a compression force to the biasing element, wherein the clip is coupled to one of the body and the drive shaft, and wherein one or more of the clip, the body and the drive shaft include a retention device that interfaces with one or more of the clip, the body and the drive shaft to prevent lateral dislodgement of the clip relative to the body and the drive shaft.

16. The assembly of claim 15, wherein the clip includes a protrusion on a face abutting the biasing element, and wherein the retention device includes the protrusion positioned in a longitudinal overlapping arrangement with the inner diameter of the biasing element.

17. The assembly of claim 15, wherein the retention device includes the clip being coupled to one of the body and the drive shaft by a resilient joint.

18. The assembly of claim 17, wherein the clip includes a clip body having a clip slot and a clip notch located in the clip slot, wherein the drive shaft includes a cantilevered tab, and wherein the resilient joint includes the cantilevered tab received in the clip notch.

19. The assembly claim 18, wherein the cantilevered tab is a resilient member.

20. The assembly of claim 15, wherein the clip is movable relative to the body along a longitudinal axis of the drive shaft.

* * * * *

UNITED STATES PATENT AND TRADEMARK OFFICE
CERTIFICATE OF CORRECTION

PATENT NO. : 11,684,380 B2
APPLICATION NO. : 16/829260
DATED : June 27, 2023
INVENTOR(S) : Butler et al.

Page 1 of 1

It is certified that error appears in the above-identified patent and that said Letters Patent is hereby corrected as shown below:

In the Claims

In Column 25, Line 31, in Claim 1, delete "a y" and insert --linearly-- therefor In Column 25, Line 55, in Claim 8, delete "dip" and insert --clip-- therefor In Column 25, Line 57, in Claim 9, delete "elements" and insert --element is-- therefor Signed and Sealed this
Twenty-ninth Day of October, 2024

Katherine Kelly Vidal
*Director of the United States Patent and Trademark Office*